(12) United States Patent
Carter et al.

(10) Patent No.: US 8,967,448 B2
(45) Date of Patent: Mar. 3, 2015

(54) SURGICAL STAPLING APPARATUS INCLUDING BUTTRESS ATTACHMENT VIA TABS

(75) Inventors: Sally Carter, Wallingford, CT (US); Richard P. Stevenson, Colchester, CT (US)

(73) Assignee: Covidien LP, Mansfield, MA (US)

( * ) Notice: Subject to any disclaimer, the term of this patent is extended or adjusted under 35 U.S.C. 154(b) by 583 days.

(21) Appl. No.: 13/325,501

(22) Filed: Dec. 14, 2011

(65) Prior Publication Data

US 2013/0153634 A1 Jun. 20, 2013

(51) Int. Cl.
*A61B 17/068* (2006.01)

(52) U.S. Cl.
USPC ....... 227/176.1; 227/19; 227/180.1; 606/139; 606/219

(58) Field of Classification Search
USPC .......... 227/19, 175.1, 176.1, 180.1; 606/139, 606/151, 153, 219
See application file for complete search history.

(56) References Cited

U.S. PATENT DOCUMENTS

| 3,054,406 | A |   | 9/1962 | Usher |
|---|---|---|---|---|
| 3,124,136 | A |   | 3/1964 | Usher |
| 4,347,847 | A |   | 9/1982 | Usher |
| 4,354,628 | A |   | 10/1982 | Green |
| 4,452,245 | A |   | 6/1984 | Usher |
| 4,473,077 | A |   | 9/1984 | Noiles et al. |
| 4,576,167 | A |   | 3/1986 | Noiles |
| 4,592,354 | A | * | 6/1986 | Rothfuss ............ 227/179.1 |
| 4,605,730 | A |   | 8/1986 | Shalaby et al. |
| 4,646,745 | A |   | 3/1987 | Noiles |
| 4,655,221 | A |   | 4/1987 | Devereux |
| 4,665,917 | A | * | 5/1987 | Clanton et al. ............ 606/153 |
| 4,834,090 | A |   | 5/1989 | Moore |
| 4,838,884 | A |   | 6/1989 | Dumican et al. |
| 4,927,640 | A |   | 5/1990 | Dahlinder et al. |

(Continued)

FOREIGN PATENT DOCUMENTS

| CA | 2 667 434 | 5/2008 |
|---|---|---|
| DE | 1 99 24 311 A1 | 11/2000 |

(Continued)

OTHER PUBLICATIONS

Extended European Search Report corresponding to EP 13 19 5919.9, completed Feb. 10, 2014 and mailed Mar. 3, 2014; (7 pp).

(Continued)

*Primary Examiner* — Scott A. Smith

(57) ABSTRACT

An apparatus for joining two hollow organ sections with an annular array of surgical staples includes a staple cartridge component, an anvil component, a buttress component and a fastening member. The staple cartridge component includes a plurality of surgical staples arranged in an annular array. The anvil component is movable relative to the staple cartridge component between spaced apart and approximated positions to adjustably clamp the organ sections between the staple cartridge and anvil components. The buttress components are configured and dimensioned to be positioned on a distal surface of the staple cartridge component and the proximal surface of the anvil component. In particular, the buttress component includes a buttress member and a plurality of circumferentially arranged tabs extending proximally from the buttress member. The fastening member is configured and dimensioned to engage the plurality of circumferentially arranged tabs to securely position the buttress component on the staple cartridge component.

8 Claims, 12 Drawing Sheets

(56) References Cited

U.S. PATENT DOCUMENTS

| | | |
|---|---|---|
| 4,930,674 A | 6/1990 | Barak |
| 5,002,551 A | 3/1991 | Linsky et al. |
| 5,005,749 A | 4/1991 | Aranyi |
| 5,014,899 A | 5/1991 | Presty et al. |
| 5,040,715 A | 8/1991 | Green et al. |
| 5,065,929 A | 11/1991 | Schulze et al. |
| 5,119,983 A | 6/1992 | Green et al. |
| 5,205,459 A | 4/1993 | Brinkerhoff et al. |
| 5,263,629 A | 11/1993 | Trumbull et al. |
| 5,314,471 A | 5/1994 | Brauker et al. |
| 5,344,454 A | 9/1994 | Clarke et al. |
| 5,392,979 A | 2/1995 | Green et al. |
| 5,397,324 A | 3/1995 | Carroll et al. |
| 5,425,745 A | 6/1995 | Green et al. |
| 5,441,193 A | 8/1995 | Gravener |
| 5,441,507 A | 8/1995 | Wilk et al. |
| 5,443,198 A | 8/1995 | Viola et al. |
| 5,468,253 A | 11/1995 | Bezwada et al. |
| 5,503,638 A | 4/1996 | Cooper et al. |
| 5,542,594 A | 8/1996 | McKean et al. |
| 5,549,628 A | 8/1996 | Cooper et al. |
| 5,575,803 A | 11/1996 | Cooper et al. |
| 5,588,579 A | 12/1996 | Schnut et al. |
| 5,653,756 A | 8/1997 | Clarke et al. |
| 5,683,809 A | 11/1997 | Freeman et al. |
| 5,690,675 A | 11/1997 | Sawyer et al. |
| 5,702,409 A | 12/1997 | Rayburn et al. |
| 5,752,965 A | 5/1998 | Francis et al. |
| 5,762,256 A | 6/1998 | Mastri et al. |
| 5,766,188 A | 6/1998 | Igaki |
| 5,769,892 A | 6/1998 | Kingwell |
| 5,782,396 A | 7/1998 | Mastri et al. |
| 5,799,857 A | 9/1998 | Robertson et al. |
| 5,810,855 A | 9/1998 | Rayburn et al. |
| 5,814,057 A | 9/1998 | Oi et al. |
| 5,833,695 A | 11/1998 | Yoon |
| 5,843,096 A | 12/1998 | Igaki et al. |
| 5,895,412 A | 4/1999 | Tucker |
| 5,895,415 A | 4/1999 | Chow et al. |
| 5,902,312 A | 5/1999 | Frater et al. |
| 5,908,427 A | 6/1999 | McKean et al. |
| 5,915,616 A | 6/1999 | Viola et al. |
| 5,931,847 A | 8/1999 | Bittner et al. |
| 5,964,774 A | 10/1999 | McKean et al. |
| 5,997,895 A | 12/1999 | Narotam et al. |
| 6,019,791 A | 2/2000 | Wood |
| 6,030,392 A | 2/2000 | Dakov et al. |
| 6,032,849 A | 3/2000 | Mastri et al. |
| 6,045,560 A | 4/2000 | McKean et al. |
| 6,053,390 A | 4/2000 | Green et al. |
| 6,063,097 A | 5/2000 | Oi et al. |
| 6,080,169 A | 6/2000 | Turtel |
| 6,099,551 A | 8/2000 | Gabbay |
| 6,149,667 A | 11/2000 | Hovland et al. |
| 6,155,265 A | 12/2000 | Hammerslag |
| 6,210,439 B1 | 4/2001 | Firmin et al. |
| 6,214,020 B1 | 4/2001 | Mulhauser et al. |
| 6,241,139 B1 | 6/2001 | Milliman et al. |
| 6,258,107 B1 | 7/2001 | Balazs et al. |
| 6,267,772 B1 | 7/2001 | Mulhauser et al. |
| 6,273,897 B1 | 8/2001 | Dalessandro et al. |
| 6,280,453 B1 | 8/2001 | Kugel et al. |
| 6,299,631 B1 | 10/2001 | Shalaby |
| 6,312,457 B1 | 11/2001 | DiMatteo et al. |
| 6,312,474 B1 | 11/2001 | Francis et al. |
| 6,325,810 B1 | 12/2001 | Hamilton et al. |
| 6,436,030 B2 | 8/2002 | Rehil |
| 6,454,780 B1 | 9/2002 | Wallace |
| 6,461,368 B2 | 10/2002 | Fogarty et al. |
| 6,503,257 B2 | 1/2003 | Grant et al. |
| 6,514,283 B2 | 2/2003 | DiMatteo et al. |
| 6,517,566 B1 | 2/2003 | Hovland et al. |
| 6,551,356 B2 | 4/2003 | Rousseau |
| 6,592,597 B2 | 7/2003 | Grant et al. |
| 6,638,285 B2 | 10/2003 | Gabbay |
| 6,652,594 B2 | 11/2003 | Francis et al. |
| 6,656,193 B2 | 12/2003 | Grant |
| 6,669,735 B1 | 12/2003 | Pelissier |
| 6,677,258 B2 | 1/2004 | Carroll et al. |
| 6,685,714 B2 | 2/2004 | Rousseau |
| 6,702,828 B2 | 3/2004 | Whayne |
| 6,704,210 B1 | 3/2004 | Myers |
| 6,723,114 B2 | 4/2004 | Shalaby |
| 6,726,706 B2 | 4/2004 | Dominguez |
| 6,736,823 B2 | 5/2004 | Darois et al. |
| 6,736,854 B2 | 5/2004 | Vadurro et al. |
| 6,746,458 B1 | 6/2004 | Cloud |
| 6,773,458 B1 | 8/2004 | Brauker et al. |
| 6,896,684 B2 | 5/2005 | Monassevitch et al. |
| 6,927,315 B1 | 8/2005 | Heinecke et al. |
| 6,939,358 B2 | 9/2005 | Palacios et al. |
| 6,946,196 B2 | 9/2005 | Foss |
| 6,959,851 B2 | 11/2005 | Heinrich |
| 7,060,087 B2 | 6/2006 | DiMatteo et al. |
| 7,087,065 B2 | 8/2006 | Ulmsten et al. |
| 7,108,701 B2 | 9/2006 | Evens et al. |
| 7,128,748 B2 | 10/2006 | Mooradian et al. |
| 7,141,055 B2 | 11/2006 | Abrams et al. |
| 7,147,138 B2 | 12/2006 | Shelton, IV |
| 7,160,299 B2 | 1/2007 | Baily |
| 7,232,449 B2 | 6/2007 | Sharkawy et al. |
| 7,241,300 B2 | 7/2007 | Sharkawy et al. |
| 7,307,031 B2 | 12/2007 | Carroll et al. |
| 7,311,720 B2 | 12/2007 | Mueller et al. |
| 7,377,928 B2 | 5/2008 | Zubik et al. |
| 7,434,717 B2 | 10/2008 | Shelton, IV et al. |
| 7,438,209 B1 | 10/2008 | Hess et al. |
| 7,547,312 B2 | 6/2009 | Bauman et al. |
| 7,559,937 B2 | 7/2009 | de la Torre et al. |
| 7,594,921 B2 | 9/2009 | Browning |
| 7,604,151 B2 | 10/2009 | Hess et al. |
| 7,665,646 B2 | 2/2010 | Prommersberger |
| 7,666,198 B2 | 2/2010 | Suyker et al. |
| 7,669,747 B2 | 3/2010 | Weisenburgh, II et al. |
| 7,717,313 B2 | 5/2010 | Bettuchi et al. |
| 7,722,642 B2 | 5/2010 | Williamson, IV |
| 7,744,627 B2 | 6/2010 | Orban, III et al. |
| 7,776,060 B2 | 8/2010 | Mooradian |
| 7,793,813 B2 | 9/2010 | Bettuchi |
| 7,799,026 B2 | 9/2010 | Schechter et al. |
| 7,823,592 B2 | 11/2010 | Bettuchi et al. |
| 7,824,420 B2 | 11/2010 | Eldridge et al. |
| 7,845,533 B2 | 12/2010 | Marczyk et al. |
| 7,845,536 B2 | 12/2010 | Viola et al. |
| 7,846,149 B2 | 12/2010 | Jankowski |
| 7,892,247 B2 | 2/2011 | Conston et al. |
| 7,909,224 B2 | 3/2011 | Prommersberger |
| 7,909,837 B2 | 3/2011 | Crews et al. |
| 7,938,307 B2 | 5/2011 | Bettuchi |
| 7,942,890 B2 | 5/2011 | D'Agostino et al. |
| 7,950,561 B2 | 5/2011 | Aranyi |
| 7,951,166 B2 | 5/2011 | Orban |
| 7,967,179 B2 | 6/2011 | Olson |
| 7,988,027 B2 | 8/2011 | Olson |
| 8,011,550 B2 | 9/2011 | Aranyi |
| 8,016,177 B2 | 9/2011 | Bettuchi |
| 8,016,178 B2 | 9/2011 | Olson |
| 8,028,883 B2 | 10/2011 | Stopek |
| 8,062,330 B2 | 11/2011 | Prommersberger |
| 8,083,119 B2 | 12/2011 | Prommersberger |
| 8,123,766 B2 | 2/2012 | Bauman |
| 8,123,767 B2 | 2/2012 | Bauman |
| 8,146,791 B2 | 4/2012 | Bettuchi |
| 8,157,149 B2 | 4/2012 | Olson |
| 8,157,151 B2 | 4/2012 | Ingmanson |
| 8,167,895 B2 | 5/2012 | D'Agostino |
| 8,192,460 B2 | 6/2012 | Orban |
| 8,210,414 B2 | 7/2012 | Bettuchi |
| 8,225,799 B2 | 7/2012 | Bettuchi |
| 8,225,981 B2 | 7/2012 | Criscuolo et al. |
| 8,231,043 B2 | 7/2012 | Tarinelli |
| 8,235,273 B2 | 8/2012 | Olson |
| 8,245,901 B2 | 8/2012 | Stopek |
| 8,256,654 B2 | 9/2012 | Bettuchi |

(56) References Cited

U.S. PATENT DOCUMENTS

| | | |
|---|---|---|
| 8,257,391 B2 | 9/2012 | Orban |
| 8,273,105 B2 | 9/2012 | Cohen |
| 8,276,800 B2 | 10/2012 | Bettuchi |
| 8,286,849 B2 | 10/2012 | Bettuchi |
| 8,308,042 B2 | 11/2012 | Aranyi |
| 8,308,045 B2 | 11/2012 | Bettuchi et al. |
| 8,308,046 B2 | 11/2012 | Prommersberger |
| 8,312,885 B2 | 11/2012 | Bettuchi et al. |
| 8,313,014 B2 | 11/2012 | Bettuchi |
| 8,348,126 B2 | 1/2013 | Olson |
| 8,348,130 B2 | 1/2013 | Shah |
| 8,365,972 B2 | 2/2013 | Aranyi et al. |
| 8,371,491 B2 | 2/2013 | Huitema |
| 8,371,492 B2 | 2/2013 | Aranyi |
| 8,371,493 B2 | 2/2013 | Aranyi |
| 8,393,514 B2 | 3/2013 | Shelton, IV |
| 8,408,440 B2 | 4/2013 | Olson |
| 8,413,871 B2 | 4/2013 | Racenet |
| 8,424,742 B2 | 4/2013 | Bettuchi |
| 8,453,652 B2 | 6/2013 | Stopek |
| 8,453,904 B2 | 6/2013 | Eskaros |
| 8,453,909 B2 | 6/2013 | Olson |
| 8,453,910 B2 | 6/2013 | Bettuchi |
| 8,464,925 B2 | 6/2013 | Hull et al. |
| 8,474,677 B2 | 7/2013 | Woodard, Jr. |
| 8,479,968 B2 | 7/2013 | Hodgkinson |
| 8,485,414 B2 | 7/2013 | Criscuolo et al. |
| 8,496,683 B2 | 7/2013 | Prommersberger |
| 8,511,533 B2 | 8/2013 | Viola |
| 8,512,402 B2 | 8/2013 | Marczyk |
| 8,529,600 B2 | 9/2013 | Woodard, Jr. |
| 8,540,131 B2 | 9/2013 | Swayze |
| 8,551,138 B2 | 10/2013 | Orban |
| 8,556,918 B2 | 10/2013 | Bauman |
| 8,561,873 B2 | 10/2013 | Ingmanson |
| 8,584,920 B2 | 11/2013 | Hodgkinson |
| 8,590,762 B2 | 11/2013 | Hess |
| 8,616,430 B2 | 12/2013 | Prommersberger |
| 8,631,989 B2 | 1/2014 | Aranyi |
| 8,668,129 B2 | 3/2014 | Olson |
| 8,684,250 B2 | 4/2014 | Bettuchi |
| 8,757,466 B2 | 6/2014 | Olson |
| 8,789,737 B2 | 7/2014 | Hodgkinson |
| 8,820,606 B2 | 9/2014 | Hodgkinson |
| 2002/0028243 A1 | 3/2002 | Masters |
| 2002/0091397 A1 | 7/2002 | Chen |
| 2003/0065345 A1 | 4/2003 | Weadock |
| 2003/0083676 A1 | 5/2003 | Wallace |
| 2003/0120284 A1 | 6/2003 | Palacios |
| 2003/0181927 A1 | 9/2003 | Wallace |
| 2003/0183671 A1 | 10/2003 | Mooradian et al. |
| 2003/0208231 A1 | 11/2003 | Williamson, IV et al. |
| 2004/0107006 A1 | 6/2004 | Francis et al. |
| 2004/0254590 A1 | 12/2004 | Hoffman et al. |
| 2004/0260315 A1 | 12/2004 | Dell et al. |
| 2005/0002981 A1 | 1/2005 | Lahtinen et al. |
| 2005/0021085 A1 | 1/2005 | Abrams et al. |
| 2005/0059996 A1 | 3/2005 | Bauman et al. |
| 2005/0059997 A1 | 3/2005 | Bauman et al. |
| 2005/0070929 A1 | 3/2005 | Dalessandro et al. |
| 2005/0118435 A1 | 6/2005 | DeLucia et al. |
| 2005/0143756 A1 | 6/2005 | Jankowski |
| 2005/0149073 A1 | 7/2005 | Arani et al. |
| 2006/0004407 A1 | 1/2006 | Hiles et al. |
| 2006/0135992 A1 | 6/2006 | Bettuchi |
| 2006/0173470 A1 | 8/2006 | Oray et al. |
| 2006/0178683 A1 | 8/2006 | Shimoji et al. |
| 2006/0271104 A1 | 11/2006 | Viola et al. |
| 2007/0026031 A1 | 2/2007 | Bauman et al. |
| 2007/0034669 A1 | 2/2007 | de la Torre et al. |
| 2007/0049953 A2 | 3/2007 | Shimoji et al. |
| 2007/0123839 A1 | 5/2007 | Rousseau et al. |
| 2007/0179528 A1 | 8/2007 | Soltz et al. |
| 2007/0203509 A1 | 8/2007 | Bettuchi |
| 2007/0203510 A1 | 8/2007 | Bettuchi |
| 2007/0246505 A1 | 10/2007 | Pace-Floridia et al. |
| 2008/0029570 A1 | 2/2008 | Shelton et al. |
| 2008/0082126 A1 | 4/2008 | Murray et al. |
| 2008/0110959 A1 | 5/2008 | Orban et al. |
| 2008/0125812 A1 | 5/2008 | Zubik et al. |
| 2008/0140115 A1 | 6/2008 | Stopek |
| 2008/0161831 A1 | 7/2008 | Bauman et al. |
| 2008/0161832 A1 | 7/2008 | Bauman et al. |
| 2008/0169327 A1 | 7/2008 | Shelton et al. |
| 2008/0169328 A1 | 7/2008 | Shelton |
| 2008/0169329 A1 | 7/2008 | Shelton et al. |
| 2008/0169330 A1 | 7/2008 | Shelton et al. |
| 2008/0169331 A1 | 7/2008 | Shelton et al. |
| 2008/0169332 A1 | 7/2008 | Shelton et al. |
| 2008/0169333 A1 | 7/2008 | Shelton et al. |
| 2008/0200949 A1 | 8/2008 | Hiles |
| 2008/0290134 A1 | 11/2008 | Bettuchi et al. |
| 2008/0308608 A1 | 12/2008 | Prommersberger |
| 2008/0314960 A1 | 12/2008 | Marczyk et al. |
| 2009/0001121 A1 | 1/2009 | Hess et al. |
| 2009/0001122 A1 | 1/2009 | Prommersberger et al. |
| 2009/0001123 A1 | 1/2009 | Morgan et al. |
| 2009/0001124 A1 | 1/2009 | Hess et al. |
| 2009/0001125 A1 | 1/2009 | Hess et al. |
| 2009/0001126 A1 | 1/2009 | Hess et al. |
| 2009/0001128 A1 | 1/2009 | Weisenburgh, II et al. |
| 2009/0001130 A1 | 1/2009 | Hess et al. |
| 2009/0005808 A1 | 1/2009 | Hess et al. |
| 2009/0030452 A1 | 1/2009 | Bauman et al. |
| 2009/0043334 A1 | 2/2009 | Bauman et al. |
| 2009/0076510 A1 | 3/2009 | Bell et al. |
| 2009/0076528 A1 | 3/2009 | Sgro |
| 2009/0078739 A1 | 3/2009 | Viola |
| 2009/0095791 A1 | 4/2009 | Eskaros et al. |
| 2009/0095792 A1 | 4/2009 | Bettuchi |
| 2009/0120994 A1 | 5/2009 | Murray et al. |
| 2009/0134200 A1 | 5/2009 | Tarinelli et al. |
| 2009/0206125 A1 | 8/2009 | Huitema et al. |
| 2009/0206126 A1 | 8/2009 | Huitema et al. |
| 2009/0206139 A1 | 8/2009 | Hall et al. |
| 2009/0206141 A1 | 8/2009 | Huitema et al. |
| 2009/0206142 A1 | 8/2009 | Huitema et al. |
| 2009/0206143 A1 | 8/2009 | Huitema et al. |
| 2009/0218384 A1 | 9/2009 | Aranyi |
| 2009/0277947 A1 | 11/2009 | Viola |
| 2009/0287230 A1 | 11/2009 | D'Agostino et al. |
| 2010/0012704 A1 | 1/2010 | Tarinelli Racenet et al. |
| 2010/0065606 A1 | 3/2010 | Stopek |
| 2010/0065607 A1 | 3/2010 | Orban, III et al. |
| 2010/0072254 A1 | 3/2010 | Aranyi et al. |
| 2010/0147921 A1 | 6/2010 | Olson |
| 2010/0147922 A1 | 6/2010 | Olson |
| 2010/0147923 A1 | 6/2010 | D'Agostino et al. |
| 2010/0243707 A1 | 9/2010 | Olson et al. |
| 2010/0243708 A1 | 9/2010 | Aranyi et al. |
| 2010/0243711 A1 | 9/2010 | Olson et al. |
| 2010/0249805 A1 | 9/2010 | Olson et al. |
| 2010/0264195 A1 | 10/2010 | Bettuchi |
| 2010/0282815 A1 | 11/2010 | Bettuchi et al. |
| 2011/0024476 A1 | 2/2011 | Bettuchi et al. |
| 2011/0024481 A1 | 2/2011 | Bettuchi et al. |
| 2011/0036894 A1 | 2/2011 | Bettuchi |
| 2011/0042442 A1 | 2/2011 | Viola et al. |
| 2011/0046650 A1 | 2/2011 | Bettuchi |
| 2011/0057016 A1 | 3/2011 | Bettuchi |
| 2011/0087279 A1 | 4/2011 | Shah et al. |
| 2011/0215132 A1 | 9/2011 | Aranyi |
| 2012/0074199 A1 | 3/2012 | Olson |
| 2012/0080336 A1 | 4/2012 | Shelton |
| 2012/0187179 A1 | 7/2012 | Gleiman |
| 2012/0241499 A1 | 9/2012 | Baxter |
| 2012/0273547 A1 | 11/2012 | Hodgkinson et al. |
| 2013/0037596 A1 | 2/2013 | Bear et al. |
| 2013/0105548 A1 | 5/2013 | Hodgkinson |
| 2013/0105553 A1 | 5/2013 | Racenet |
| 2013/0112732 A1 | 5/2013 | Aranyi |
| 2013/0112733 A1 | 5/2013 | Aranyi |
| 2013/0146641 A1 | 6/2013 | Shelton |
| 2013/0153633 A1 | 6/2013 | Casasanta |

(56) References Cited

U.S. PATENT DOCUMENTS

| | | |
|---|---|---|
| 2013/0153635 A1 | 6/2013 | Hodgkinson |
| 2013/0153636 A1 | 6/2013 | Shelton |
| 2013/0153638 A1 | 6/2013 | Carter |
| 2013/0153639 A1 | 6/2013 | Hodgkinson |
| 2013/0153640 A1 | 6/2013 | Hodgkinson |
| 2013/0153641 A1 | 6/2013 | Shelton |
| 2013/0161374 A1 | 6/2013 | Swayze |
| 2013/0181031 A1 | 7/2013 | Olson |
| 2013/0193186 A1 | 8/2013 | Racenet |
| 2013/0193190 A1 | 8/2013 | Carter |
| 2013/0193191 A1 | 8/2013 | Stevenson |
| 2013/0193192 A1 | 8/2013 | Casasanta |
| 2013/0209659 A1 | 8/2013 | Racenet |
| 2013/0221062 A1 | 8/2013 | Hodgkinson |
| 2013/0240600 A1 | 9/2013 | Bettuchi |
| 2013/0240601 A1 | 9/2013 | Bettuchi |
| 2013/0240602 A1 | 9/2013 | Stopek |
| 2013/0277411 A1 | 10/2013 | Hodgkinson |
| 2013/0306707 A1 | 11/2013 | Viola |
| 2013/0310873 A1 | 11/2013 | Prommersberger |
| 2013/0327807 A1 | 12/2013 | Olson |
| 2014/0012317 A1 | 1/2014 | Orban |
| 2014/0021242 A1 | 1/2014 | Hodgkinson |
| 2014/0027490 A1 | 1/2014 | Marczyk |
| 2014/0034704 A1 | 2/2014 | Ingmanson |
| 2014/0048580 A1 | 2/2014 | Merchant |
| 2014/0061280 A1 | 3/2014 | Ingmanson |
| 2014/0061281 A1 | 3/2014 | Hodgkinson |
| 2014/0084042 A1 | 3/2014 | Stopek |
| 2014/0097224 A1 | 4/2014 | Prior |
| 2014/0117066 A1 | 5/2014 | Aranyi |
| 2014/0130330 A1 | 5/2014 | Olson |
| 2014/0131418 A1 | 5/2014 | Kostrzewski |
| 2014/0131419 A1 | 5/2014 | Bettuchi |
| 2014/0138423 A1 | 5/2014 | Whitfield |
| 2014/0151431 A1 | 6/2014 | Hodgkinson |
| 2014/0155916 A1 | 6/2014 | Hodgkinson |
| 2014/0158742 A1 | 6/2014 | Stopek |
| 2014/0166721 A1 | 6/2014 | Stevenson |
| 2014/0197224 A1 | 7/2014 | Penna |
| 2014/0203061 A1 | 7/2014 | Hodgkinson |
| 2014/0217147 A1 | 8/2014 | Milliman |
| 2014/0217148 A1 | 8/2014 | Penna |
| 2014/0239046 A1 | 8/2014 | Milliman |
| 2014/0239047 A1 | 8/2014 | Hodgkinson |

FOREIGN PATENT DOCUMENTS

| | | |
|---|---|---|
| DE | 199 24 311 A1 | 11/2000 |
| EP | 0 594 148 A1 | 4/1994 |
| EP | 0 327 022 B1 | 4/1995 |
| EP | 0 667 119 A1 | 8/1995 |
| EP | 1 064 883 A1 | 1/2001 |
| EP | 1 256 317 A2 | 11/2002 |
| EP | 1 256 318 | 11/2002 |
| EP | 1 520 525 A1 | 4/2005 |
| EP | 1 621 141 A2 | 2/2006 |
| EP | 1 702 570 A1 | 9/2006 |
| EP | 1 759 640 A2 | 3/2007 |
| EP | 1 815 804 A2 | 8/2007 |
| EP | 1 825 820 | 8/2007 |
| EP | 1 929 958 | 6/2008 |
| EP | 1 994 890 A1 | 11/2008 |
| EP | 2 005 894 A2 | 12/2008 |
| EP | 2 005 895 A2 | 12/2008 |
| EP | 2 008 595 A2 | 12/2008 |
| EP | 2 090 231 | 8/2009 |
| EP | 2 090 244 | 8/2009 |
| EP | 2 090 252 | 8/2009 |
| EP | 2 198 787 A1 | 6/2010 |
| EP | 2 236 098 A2 | 10/2010 |
| EP | 2 236 099 | 10/2010 |
| EP | 2 311 386 | 4/2011 |
| EP | 2 436 348 | 4/2012 |
| EP | 2 462 880 | 6/2012 |
| EP | 2 517 637 | 10/2012 |
| EP | 2 586 380 | 5/2013 |
| EP | 2 604 195 | 6/2013 |
| EP | 2 604 197 | 6/2013 |
| EP | 2 620 106 | 7/2013 |
| EP | 2 630 922 | 8/2013 |
| EP | 2 644 125 | 10/2013 |
| JP | 2000-166933 | 6/2000 |
| JP | 2002-202213 | 7/2002 |
| JP | 07-124166 | 5/2007 |
| WO | WO 90/05489 A1 | 5/1990 |
| WO | WO 95/16221 | 6/1995 |
| WO | WO 96/22055 A1 | 7/1996 |
| WO | WO 97/01989 A1 | 1/1997 |
| WO | WO 97/13463 A1 | 4/1997 |
| WO | WO 98/17180 A1 | 4/1998 |
| WO | WO 99/45849 A1 | 9/1999 |
| WO | WO 03/082126 A1 | 10/2003 |
| WO | WO 03/088845 | 10/2003 |
| WO | WO 03/094743 | 11/2003 |
| WO | WO 03/105698 A2 | 12/2003 |
| WO | WO 2005/079675 | 9/2005 |
| WO | WO 2006/023578 A2 | 3/2006 |
| WO | WO 2006/044490 A2 | 4/2006 |
| WO | WO 2006/083748 A1 | 8/2006 |
| WO | WO 2007/121579 A1 | 11/2007 |
| WO | WO 2008/057281 A2 | 5/2008 |
| WO | WO 2008/109125 A1 | 9/2008 |
| WO | WO 2010/075298 A2 | 7/2010 |
| WO | WO 2011/143183 A2 | 11/2011 |
| WO | WO 2012/044848 A1 | 4/2012 |

OTHER PUBLICATIONS

Extended European Search Report corresponding to EP No. 12 19 1035.0, completed Jan. 11, 2013 and mailed Jan. 18, 2013; 7 pages.
Extended European Search Report corresponding to EP No. 12 18 6175.1, completed Jan. 15, 2013 and mailed Jan. 23, 2013; 7 pages.
Extended European Search Report corresponding to EP No. 12 19 1114.3, completed Jan. 23, 2013 and mailed Jan. 31, 2013; 10 pages.
Extended European Search Report corresponding to EP No. 12 19 2224.9, completed Mar. 14, 2013 and mailed Mar. 26, 2013; 8 pages.
Extended European Search Report corresponding to EP No. 12 19 6911.7, completed Apr. 18, 2013 and mailed Apr. 24, 2013; 8 pages.
International Search Report corresponding to European Application No. EP 12 15 2229.6, completed on Feb. 23, 2012 and mailed on Mar. 1, 2012; 4 pages.
International Search Report corresponding to European Application No. EP 12 15 0511.9, completed on Apr. 16, 2012 and mailed on Apr. 24, 2012; 7 pages.
International Search Report corresponding to European Application No. EP 12 15 2541.4, completed on Apr. 23, 2012 and mailed on May 3, 2012; 10 pages.
International Search Report corresponding to European Application No. EP 12 16 5609.4, completed on Jul. 5, 2012 and mailed on Jul. 13, 2012; 8 pages.
International Search Report corresponding to European Application No. EP 12 15 8861.0, completed on Jul. 17, 2012 and mailed on Jul. 24, 2012; 9 pages.
International Search Report corresponding to European Application No. EP 12 16 5878.5, completed on Jul. 24, 2012 and mailed on Aug. 6, 2012; 8 pages.
Extended European Search Report corresponding to EP 12 19 1035.0, completed Jan. 11, 2013 and mailed Jan. 18, 2013; 7 pages.
Extended European Search Report corresponding to EP 12 19 6904.2, completed Mar. 28, 2013 and mailed Jul. 26, 2013; 8 pages.
Extended European Search Report corresponding to EP 12 19 8749.9, completed May 21, 2013 and mailed May 31, 2013; 8 pages.
Extended European Search Report corresponding to EP 07 00 5842.5, completed May 13, 2013 and mailed May 29, 2013; 7 pages.
Extended European Search Report corresponding to EP 12 19 8776.2, completed May 16, 2013 and mailed May 27, 2013; 8 pages.
Extended European Search Report corresponding to EP 13 15 6297.7, completed Jun. 4, 2013 and mailed Jun. 13, 2013; 7 pages.
Extended European Search Report corresponding to EP 13 17 3985.6, completed Aug. 19, 2013 and mailed Aug. 28, 2013; 6 pages.

(56) References Cited

OTHER PUBLICATIONS

Extended European Search Report corresponding to EP 13 17 3986.4, completed Aug. 20, 2013 and mailed Aug. 29, 2013; 7 pages.
Extended European Search Report corresponding to EP 13 17 7437.4, completed Sep. 11, 2013 and mailed Sep. 19, 2013; (6 pp).
Extended European Search Report corresponding to EP 13 17 7441.6, completed Sep. 11, 2013 and mailed Sep. 19, 2013; (6 pp).
Extended European Search Report corresponding to EP 07 86 1534.1, completed Sep. 20, 2013 and mailed Sep. 30, 2013; (5 pp).
Extended European Search Report corresponding to EP 13 18 3876.5, completed Oct. 14, 2013 and mailed Oct. 24, 2013; (5 pp).
Extended European Search Report corresponding to EP 13 17 1856.1, completed Oct. 29, 2013 and mailed Nov. 7, 2013; (8 pp).
Extended European Search Report corresponding to EP 13 18 0373.6, completed Oct. 31, 2013 and mailed Nov. 13, 2013; (7 pp).
Extended European Search Report corresponding to EP 13 18 0881.8, completed Nov. 5, 2013 and mailed Nov. 14, 2013; (6 pp).
Extended European Search Report corresponding to EP 13 17 6895.4, completed Nov. 29, 2013 and mailed Dec. 12, 2013; (5 pp).
Extended European Search Report corresponding to EP 13 18 2911.1, completed Dec. 2, 2013 and mailed Dec. 16, 2013; (8 pp).
Extended European Search Report corresponding to EP 10 25 1795.0, completed Dec. 11, 2013 and mailed Dec. 20, 2013; (6 pp).
Extended European Search Report corresponding to EP 13 18 7911.6, completed Jan. 22, 2014 and mailed Jan. 31, 2014; (8 pp).
International Search Report corresponding to European Application No. EP 05 02 2585.3, completed on Jan. 25, 2006 and mailed on Feb. 3, 2006; 4 pages.
International Search Report corresponding to European Application No. EP 06 00 4598, completed on Jun. 22, 2006; 2 pages.
International Search Report corresponding to European Application No. EP 06 01 6962.0, completed on Jan. 3, 2007 and mailed on Jan. 11, 2007; 10 pages.
International Search Report corresponding to International Application No. PCT/US05/36740, completed on Feb. 20, 2007 and mailed on Mar. 23, 2007; 8 pages.
International Search Report corresponding to International Application No. PCT/US2007/022713, completed on Apr. 21, 2008 and mailed on May 15, 2008; 1 page.
International Search Report corresponding to International Application No. PCT/US2008/002981, completed on Jun. 9, 2008 and mailed on Jun. 26, 2008; 2 pages.
International Search Report corresponding to European Application No. EP 08 25 1779, completed on Jul. 14, 2008 and mailed on Jul. 23, 2008; 5 pages.
International Search Report corresponding to European Application No. EP 08 25 1989.3, completed on Mar. 11, 2010 and mailed on Mar. 24, 2010; 6 pages.
International Search Report corresponding to European Application No. EP 10 25 0639.1, completed on Jun. 17, 2010 and mailed on Jun. 28, 2010; 7 pages.
International Search Report corresponding to European Application No. EP 10 25 0715.9, completed on Jun. 30, 2010 and mailed on Jul. 20, 2010; 3 pages.
International Search Report corresponding to European Application No. EP 05 80 4382.9, completed on Oct. 5, 2010 and mailed on Oct. 12, 2010; 3 pages.
International Search Report corresponding to European Application No. EP 10 25 1437.9, completed on Nov. 22, 2010 and mailed on Dec. 16, 2010; 3 pages.
International Search Report corresponding to European Application No. EP 09 25 2897.5, completed on Feb. 7, 2011 and mailed on Feb. 15, 2011; 3 pages.
International Search Report corresponding to European Application No. EP 10 25 0642.5, completed on Mar. 25, 2011 and mailed on Apr. 4, 2011; 4 pages.
International Search Report corresponding to European Application No. EP 11 18 8309.6, completed on Dec. 15, 2011 and mailed on Jan. 12, 2012; 3 pages.
Extended European Search Report corresponding to EP 13 19 2123.1, completed Jan. 30, 2014 and mailed Feb. 10, 2014; (8 pp).
Extended European Search Report corresponding to EP 13 19 2111.6, completed Feb. 13, 2014 and mailed Feb. 27, 2014; (10 pp).
Extended European Search Report corresponding to EP 08 72 6500.5, completed Feb. 20, 2014 and mailed Mar. 3, 2014; (7 pp).
Extended European Search Report corresponding to EP 13 19 5019.8, completed Mar. 14, 2014 and mailed Mar. 24, 2014; (7 pp).
Extended European Search Report corresponding to EP 13 19 6816.6, completed Mar. 28, 2014 and mailed Apr. 9, 2014; (9 pp).
Extended European Search Report corresponding to EP 13 19 7958.5, completed Apr. 4, 2014 and mailed Apr. 15, 2014; (8 pp).
Extended European Search Report corresponding to EP 13 19 4995.0, completed Jun. 5, 2014 and mailed Jun. 16, 2014; (5 pp).
Extended European Search Report corresponding to EP 14 15 7195.0, completed Jun. 5, 2014 and mailed Jun. 18, 2014; (9 pp).
Extended European Search Report corresponding to EP 14 15 6342.9, completed Jul. 22, 2014 and mailed Jul. 29, 2014; (8 pp).

\* cited by examiner

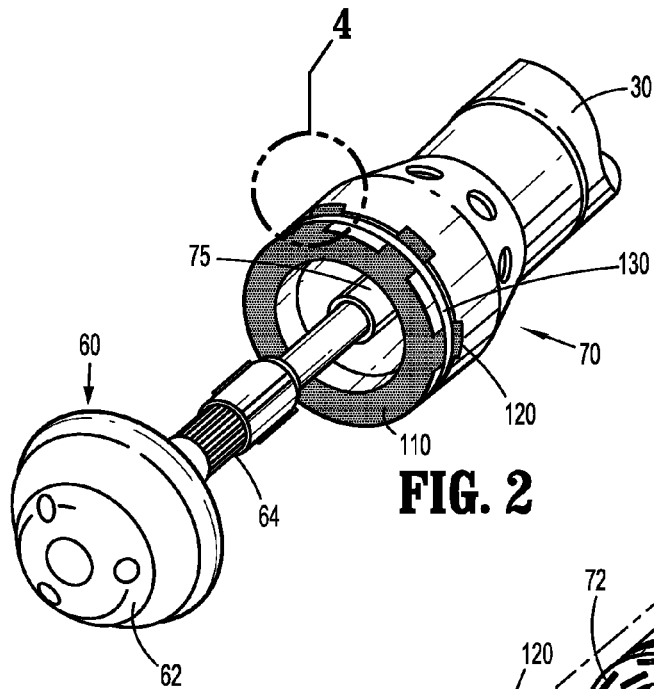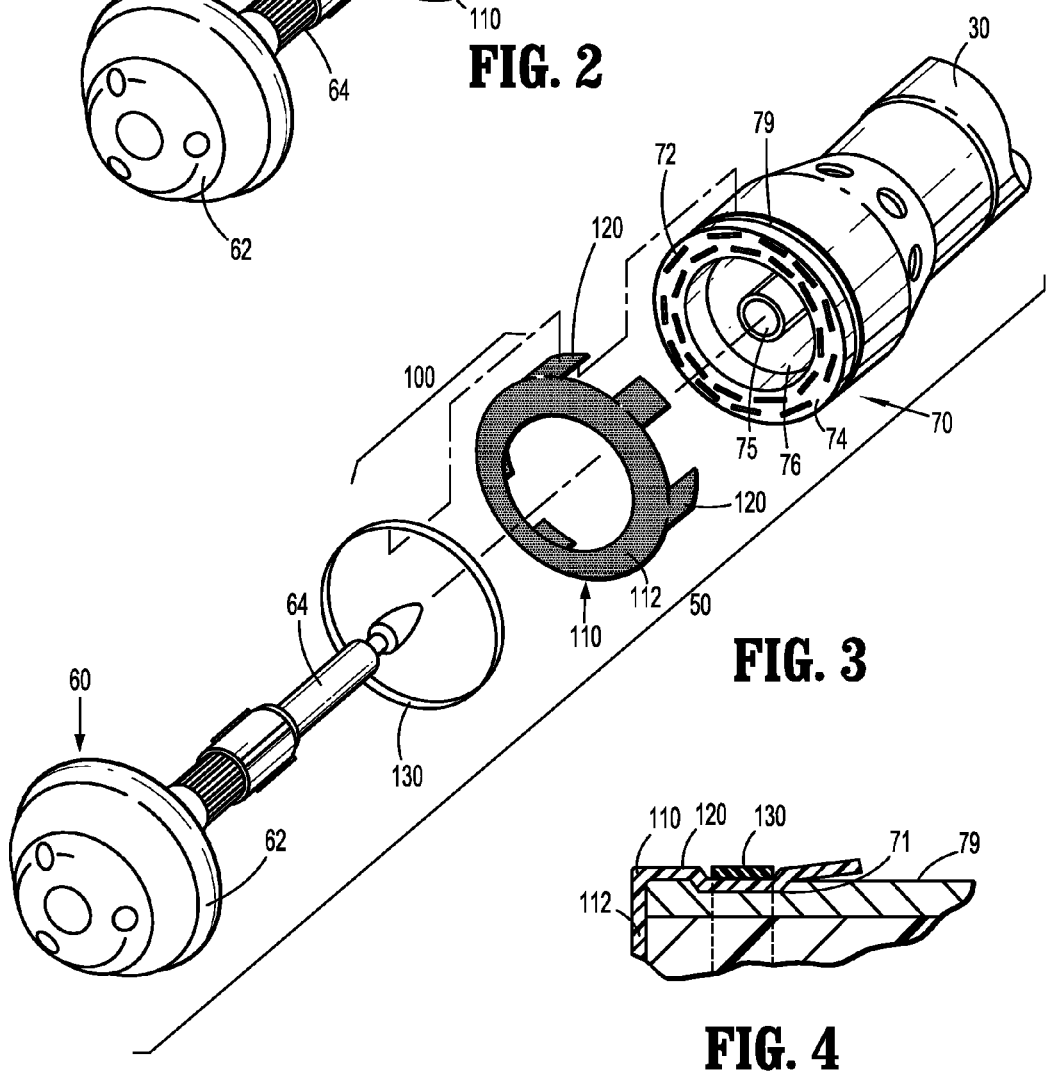

SURGICAL STAPLING APPARATUS INCLUDING BUTTRESS ATTACHMENT VIA TABS

BACKGROUND

1. Technical Field

The present disclosure relates to a surgical instrument for applying surgical fasteners or staples to body tissue, and more particularly, to a surgical buttress for use with an end-to-end anastomosis stapling apparatus.

2. Background of Related Art

Anastomosis is a surgical joining of separate hollow organ sections. Typically, an anastomosis procedure follows surgery in which a diseased or defective section of hollow tissue is removed and the remaining end sections are joined. Depending on the desired anastomosis procedure, the end sections may be joined by either circular, end-to-end or side-to-side organ reconstruction methods.

In a circular anastomosis procedure, the two ends of the organ sections are joined by means of a stapling instrument, which drives a circular array of staples through the end section of each organ section and simultaneously cores any tissue interior of the driven circular array of staples to free the tubular passage. Typically, these instruments include an elongated shaft having a handle portion at a proximal end to actuate the instrument and a staple holding component disposed at a distal end. An anvil assembly including an anvil shaft with attached anvil head is mounted to the distal end adjacent the staple holding component. Opposed end sections of the organ to be stapled are clamped between the anvil head and the staple holding component. The clamped tissue is stapled by driving a plurality of staples from the staple holding component so that the ends of the staples pass through the tissue and are deformed by the anvil head.

In use, one end section of the organ is secured about the anvil assembly and the other end section of the organ is held in place adjacent the staple holding component. The shaft of the anvil assembly is removably connected to the instrument. Once the anvil shaft is secured to the instrument, the anvil is drawn into close approximation to the staple holding component. The instrument is then fired to cause the staples to pass through tissue of both sections of the organ and deform against the anvil. During the firing step, a circular knife is advanced to cut tissue inside the staple line, thereby establishing a passage between the two sections of the organ. After firing, the instrument is typically removed by withdrawing the anvil through the staple line, after which the surgeon will carefully inspect the surgical site to ensure a proper anastomosis has been achieved.

While circular staplers are helpful in a number of surgical procedures, problems such as anastomotic leak, tear of tissue during stapler extraction, bleeding, and other complications may arise. In order to remedy such problems, buttress or reinforcing materials have been utilized. However, due to the inherent difficulty in positioning and securing such materials with the instrument, there is a continuing need for buttress material and buttress material and instrument combinations that can be safely and effectively positioned within staple cartridge and/or anvil.

SUMMARY

In accordance with an embodiment of the present disclosure, there is provided an apparatus for joining two hollow organ sections with an annular array of surgical staples. The apparatus includes a staple cartridge component, an anvil component, a buttress component, and a fastening member. The staple cartridge component includes a plurality of surgical staples arranged in an annular array. The anvil component is movable relative to the staple cartridge component between spaced apart and approximated positions to adjustably clamp the organ sections between the staple cartridge and anvil components. The buttress component is configured and dimensioned to be positioned on a distal surface of the staple cartridge component. The buttress component includes a buttress member and a plurality of circumferentially arranged tabs extending proximally from the buttress member. The fastening member is configured and dimensioned to engage the plurality of circumferentially arranged tabs to securely position the buttress component on the staple cartridge component.

In an embodiment, the buttress member may have an annular configuration. In particular, the buttress member may be concentrically disposed in a juxtaposed relation with the plurality of surgical staples. The fastening member may be an annular ring configured and dimensioned to apply inward force to the plurality of circumferentially arranged tabs against an outer wall of the staple cartridge component. In addition, the fastening member may be a suture tied around the plurality of circumferentially arranged tabs against an outer wall of the staple cartridge component.

In another embodiment, the outer wall of the staple cartridge component may define a circumferential groove configured and adapted to receive a portion of the plurality of circumferentially arranged tabs. The fastening member may be in registration with the circumferential groove.

The apparatus may further include a knife member concentrically arranged in the staple cartridge component and with the buttress member. The knife member may be movable relative to the staple cartridge component. In particular, the buttress member may be configured to be disposed radially outward of knife member.

The plurality of circumferentially arranged tabs may each define a line of weakening adjacent the buttress member to enable detachment of the buttress member from the plurality of tabs. The buttress component may be configured such that the plurality of circumferentially arranged tabs engage an inner wall of the staple cartridge component.

In accordance with another embodiment of the present disclosure, there is provided an apparatus for joining two hollow organ sections with an annular array of surgical staples. The apparatus includes a staple cartridge component, an anvil component, a buttress component, and a fastening member. The staple cartridge component includes a plurality of surgical staples in an annular array. The anvil component is movable relative to the staple cartridge component between spaced apart and approximated positions to adjustably clamp the organ sections between the staple cartridge and anvil components. The buttress component is configured and dimensioned to be positioned on a distal surface of the staple cartridge component. In particular, the buttress component includes a buttress member and an outer rim extending proximally from the buttress member. The outer rim is configured and adapted to engage an outer wall of the staple cartridge component. The fastening member is tied around the outer rim of the buttress component to secure the outer rim against the outer wall of the staple cartridge component.

In an embodiment, the outer rim may include a plurality of circumferentially arranged loops configured and adapted to receive the fastening member therethrough. Alternatively, the outer rim may define a plurality of circumferentially arranged apertures dimensioned to receive the fastening member therethrough. Furthermore, each aperture may include an adhesive to secure the fastening member therein. The outer rim may define a circumferential line of weakening adjacent the buttress member to enable detachment of the buttress member from the outer rim.

In accordance with still another embodiment of the present disclosure, there is provided an apparatus for joining two hollow organ sections with an annular array of surgical staples. The apparatus includes a staple cartridge component, an anvil component, a knife member and a buttress component. The staple cartridge component includes a plurality of surgical staples in an annular array. The anvil component defines a plurality of staple pockets for forming the surgical staples. The anvil component is movable relative to the staple cartridge component between spaced apart and approximated positions to adjustably clamp the organ sections between the staple cartridge and anvil components. The knife member is concentrically arranged in the staple cartridge component. The knife member is movable relative to the staple cartridge component. The buttress component includes a buttress member concentrically aligned with the plurality of surgical staples and a plurality of circumferentially arranged tabs extending proximally from the buttress member. The plurality of tabs and the staple cartridge component have corresponding attaching members for securing the plurality of tabs to the staple cartridge component.

In an embodiment, the attaching members may be hook and loop fasteners. In particular, the staple cartridge component may have the hook and loop fasteners on the outer wall thereof and the plurality of tabs may have the corresponding hook and loop fasteners on an inner surface of thereof. Alternatively, the staple cartridge component may have the hook and loop fasteners on an inner wall thereof and the plurality of tabs may have the corresponding hook and loop fasteners on an outer surface of thereof.

In accordance with yet another embodiment of the present disclosure, there is provided an apparatus for joining two hollow organ sections with an annular array of surgical staples. The apparatus includes a staple cartridge component, an anvil component, a knife member and a first buttress component. The staple cartridge component includes a plurality of surgical staples in an annular array. The anvil component includes an anvil member defining a plurality of staple pockets for forming the surgical staples and a shaft extending distally from the anvil member. The anvil component is movable relative to the staple cartridge component between spaced apart and approximated positions to adjustably clamp the organ sections between the staple cartridge and anvil components. The knife member is concentrically arranged in the staple cartridge component. The knife member is movable relative to the staple cartridge component. The first buttress component includes a buttress member concentrically aligned with the anvil component and a rim extending distally from the buttress member. The first buttress component encloses the plurality of staple pockets defined in the anvil member.

The apparatus may further include a fastening member securing the first buttress component to the shaft of the anvil component. In particular, the fastening member may include a plurality of barbs. The rim of the first buttress component may be an outer rim that engages an outer surface of the anvil member. In addition, the first buttress component may further include an inner rim extending distally from the buttress member. The inner rim may be configured and dimensioned to engage the shaft of the anvil component.

In an embodiment, the apparatus may further include a second buttress component concentrically aligned with the staple cartridge component. The second buttress component may include a buttress member and a plurality of circumferentially arranged tabs extending proximally from the buttress member. The plurality of tabs may engage an outer wall of the staple cartridge component. In particular, the plurality of tabs and the outer wall of the staple cartridge component may include corresponding hook and loop fasteners to secure the second buttress component to the staple cartridge component.

Each tab may include a line of weakening adjacent the buttress member for detachment of the buttress member from the plurality of tabs. The buttress component may be configured such that the plurality of tabs engage an inner wall of the staple cartridge component. The plurality of tabs and the inner wall of the staple cartridge component may include corresponding hook and loop fasteners to secure the second buttress component to the staple cartridge component.

The apparatus may further include a fastening member configured and dimensioned to engage the plurality of circumferentially arranged tabs to securely position the second buttress component on the staple cartridge component. The fastening member may be an annular ring configured and dimensioned to apply inward force to the plurality of circumferentially arranged tabs against an outer wall of the staple cartridge component. Alternatively, the fastening member may be a suture tied around the plurality of circumferentially arranged tabs against an outer wall of the staple cartridge component.

BRIEF DESCRIPTION OF THE DRAWINGS

Various embodiments of the present disclosure are described hereinbelow with reference to the drawings, wherein:

FIG. 2 is a perspective view of a head portion of the surgical stapling apparatus of FIG. 1 illustrating a surgical buttress assembly mounted on a distal portion of a staple cartridge assembly;

FIG. 3 is an exploded, perspective view, with parts separated, of the head portion of FIG. 2;

FIG. 4 is an enlarged, cross-sectional view of the area of detail indicated in FIG. 2;

DETAILED DESCRIPTION OF EMBODIMENTS

Figure 1:
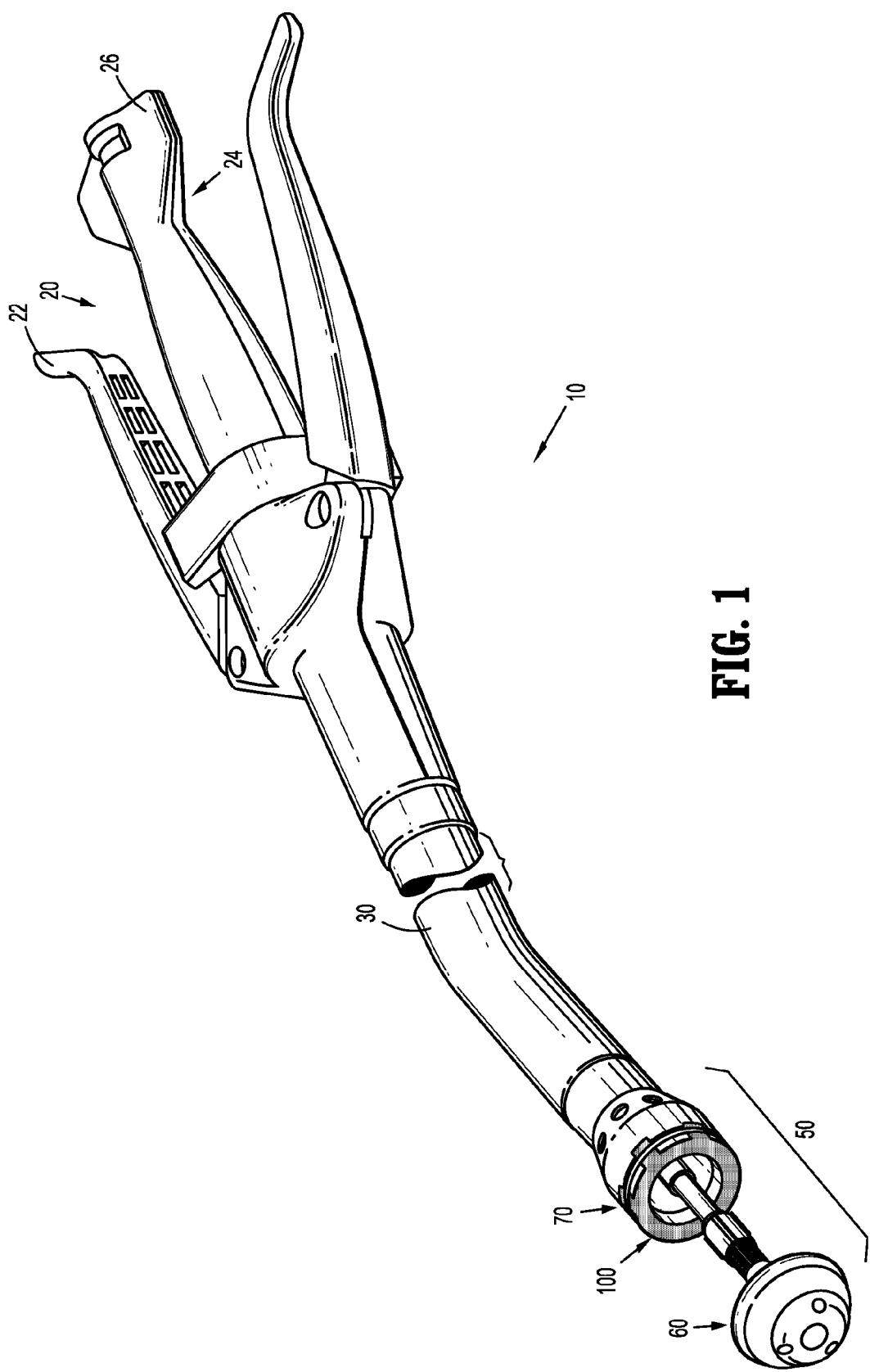
FIG. 1 is a perspective view of an annular surgical stapling apparatus configured for use with a surgical buttress assembly in accordance with an embodiment of the present disclosure.

Embodiments of the present disclosure will now be described in detail with reference to the drawings, in which like reference numerals designate identical or corresponding elements in each of the several views. As used herein, the term "distal," as is conventional, will refer to that portion of the instrument, apparatus, device or component thereof which is farther from the user while, the term "proximal," will refer to that portion of the instrument, apparatus, device or component thereof which is closer to the user. In the following description, well-known functions or constructions are not described in detail to avoid obscuring the present disclosure in unnecessary detail.

With reference to FIG. 1, a surgical stapling apparatus 10 for performing circular anastomosis of hollow organs is shown. Surgical stapling apparatus 10 drives a circular array of staples 7 (FIG. 9) through the end sections of each organ and simultaneously fires a cylindrical knife 76 (FIG. 9) to cores any tissue radially inward of the driven circular array of staples 7 to free the tubular passage, and thereby joining two ends of the organ. Surgical stapling apparatus 10 includes a handle assembly 20 having a pair of pivotable actuating handle members 22 and an advancing means 24 including a rotatable grip member 26, an elongate body portion 30 extending distally from handle assembly 20, and a head portion 50 including an anvil assembly 60, a staple cartridge assembly 70, and a surgical buttress assembly 100 in accordance with an embodiment of the present disclosure.

The components of surgical apparatus 10 are generally formed from thermoplastics including polycarbonates, and metals including stainless steel and aluminum. The particular material selected to form a particular component will depend upon the strength requirements of the particular component. Staples 7 are of a conventional type and include a backspan having a pair of legs extending from the backspan. The legs terminate in tissue penetrating tips.

Handle assembly 20 can be actuated to approximate anvil assembly 60 relative to staple cartridge assembly 70 and to apply a pair of annular arrays of staples 7 through tissue. In order to properly position tissue in head portion 50, rotatable grip member 26 may be rotated to move anvil assembly 60 axially relative to staple cartridge assembly 70 between a spaced apart position and an approximated position in which anvil assembly 60 is positioned adjacent staple cartridge assembly 70 to clamp tissue therebetween. Handle members 22 may be squeezed to fire staples 7 through tissue to join two segments "$T_1$," "$T_2$" (FIG. 9) of tubular tissues together, as will be discussed in detail below.

Elongate body portion 30 is constructed to have a slightly curved/bent shape along its length. However, elongate body portion 30 may also be straight, as well as flexible to bend to any configuration. The length, shape and/or the diameter of elongate body portion 30 may be varied to suit a particular surgical procedure.

With reference to FIGS. 2-4, head portion 50 includes anvil assembly 60, staple cartridge assembly 70 and surgical buttress assembly 100 detachably secured with staple cartridge assembly 70. Staple cartridge assembly 70 may be fixedly connected to a distal end portion of elongate body portion 30 or may be configured to concentrically fit within the distal end portion of elongate body portion 30. In particular, staple cartridge assembly 70 defines a pair of annular arrays of staple receiving slots 72 having a staple 7 disposed in each one of staple receiving slots 72 and a circumferentially arranged groove 71 (FIG. 4) such as, e.g., a countersink, in an outer wall 79 thereof.

In addition, staple cartridge assembly 70 includes cylindrical knife 76 concentrically arranged with the pair of annular arrays of staples 7 and a plurality of staple pushers 9 (FIG. 9) each disposed in respective staple receiving slot 72 to eject the respective staple 7 through slot 72. In use, staples 7 travel through slots 72 and tissue toward anvil assembly 60 for formation thereof.

Figure 9:
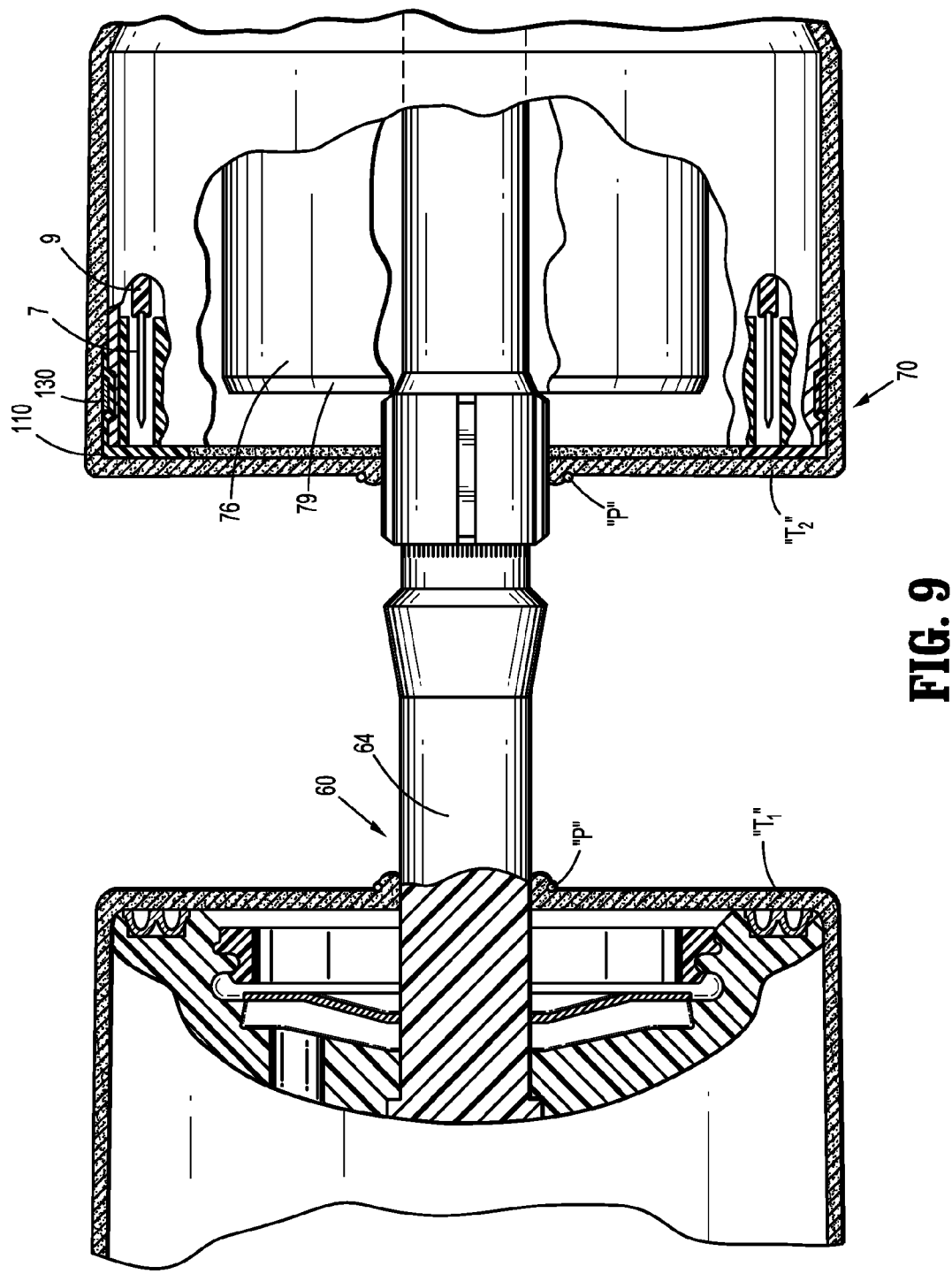
FIG. 9 is an enlarged, partial longitudinal, cross-sectional view of the head portion of the apparatus of FIG. 8.

With brief reference to FIG. 9, cylindrical knife 76 includes a distal rim 79 defining a knife blade adapted to cut tissue. Upon actuation of handle members 22, cylindrical knife 76 is moved distally to cut tissue, and the plurality of pushers 9 are moved distally to eject staples 7 disposed in staple receiving slots 72 therethrough, toward anvil assembly 60.

With particular reference back to FIG. 3, positioned distally of staple cartridge assembly 70 is anvil assembly 60 including an anvil member 62 and a shaft 64 extending proximally from anvil member 62. Anvil member 62 includes a plurality of pockets (not shown) for receiving and forming staples 7. Shaft 64 is configured to be detachably received in approximation shaft 75 disposed in elongate body portion 30. Approximation shaft 75 is operatively coupled with rotatable grip member 26 of handle assembly 20, whereby rotation of rotatable grip member 26 moves approximation shaft 75 axially. Such axial movement of approximation shaft 75 is imparted to anvil assembly 60 detachably coupled with approximation shaft 75. In this manner, anvil assembly 60 is movable axially relative to staple cartridge assembly 70 between a spaced apart position and an approximated position in which anvil assembly 60 is positioned adjacent staple cartridge assembly 70 to adjustably clamp tissue between anvil assembly 60 and staple cartridge assembly 70.

Examples of instruments for performing circular anastomosis of hollow organs are described in U.S. Pat. Nos. 6,053,390, 5,588,579, 5,119,983, 5,005,749, 4,646,745, 4,576,167, and 4,473,077, each of which is hereby incorporated herein in its entirety by reference.

With continued reference to FIGS. 3 and 4, surgical buttress assembly 100 includes a buttress component 110 and a fastening member in the form of an annular ring 130 configured and dimensioned to secure buttress component 110 on staple cartridge assembly 70. Buttress component 110 is provided to reinforce and seal staple lines applied to tissue by surgical stapling apparatus 10.

Buttress component 110 includes a buttress member 112 having an annular profile configured to be concentrically aligned with staple cartridge assembly 70 and a plurality of circumferentially arranged tabs 120 extending proximally from buttress member 112. In use, buttress member 112 is mounted on a distal surface 74 of staple cartridge assembly 70. The annular profile of buttress member 112 is configured and dimensioned to be flush with an outer peripheral edge of staple cartridge assembly 70 when mounted on staple cartridge assembly 70. Moreover, buttress member 112 is superposed with the pair of annular arrays of staple receiving slots 72. In this manner, when staples 7 are ejected through the pair of annular arrays of staple receiving slots 72, the legs of each staple 7 penetrate through buttress member 112 and the backspan of staple 7 is secured or abuts against a proximal surface of buttress member 112.

In addition, cylindrical knife 76 is disposed radially inward of annular array of staple receiving slots 72 and of buttress member 112 that is in a superposed relation with the annular array of staple receiving slots 72 so as to not extend across a knife path of cylindrical knife 76. In this manner, upon actuation of handle members 22, the entire buttress member 112 is stapled to tissue to reinforce said tissue, and severing of buttress member 112 by cylindrical knife 76 is eliminated.

A fastening member is configured and dimensioned to engage the plurality of circumferentially arranged tabs to securely position the buttress component on the staple cartridge component of the stapling apparatus. For example, the plurality of circumferentially arranged tabs 120 that extend proximally from buttress member 112 are positionable on distal surface 74 of cartridge assembly 70. See FIG. 3. More particularly, a proximal end of each tab 120 extends proximal of a groove 71 circumferentially defined in outer wall 79 of cartridge assembly 70. See FIG. 4.

The fastening member may be provided in the form of an annular ring 130, which is secured around circumferentially arranged tabs 120, such that annular ring 130 applies a radially inward force against tabs 120 disposed across groove 71. In this manner, annular ring 130 overlies groove 71 and is substantially flush with portions of buttress member 112 and/or tabs 120 that are disposed on or against outer wall 79 of staple cartridge assembly 70. Such configuration enables buttress member 112 to be securely positioned in place with respect to staple cartridge assembly 70.

Annular ring 130 may include and is not limited to a resilient band. For example, a piece of spring metal, which may be circular in shape, or a length of suture material, or similar straps, bands, cables, or other members may be used.

Buttress component 110 is monolithically formed as a single construct. However, each tab 120 may include a break, perforations, or a line of weakening adjacent buttress member 112, whereby buttress member 112 that is stapled to tissue may be severed or detached from the plurality of tabs 120. In this manner, tabs 120 may at least partially be retained in groove 71 by annular ring 130 and later removed from the surgical site along with surgical stapling apparatus 10.

Buttress member 112 is fabricated from a biocompatible material which is bio-absorbable or non-absorbable, as well as natural or synthetic materials. It should be understood that any combination of natural, synthetic, bio-absorbable, and non-bioabsorbable materials may be used to form buttress member 112.

In addition, buttress member 112 may be porous, non-porous, or combinations thereof. It is also envisioned that buttress member 112 described herein may contain a plurality of layers in which any combination of non-porous and porous layers may be configured. For example, buttress member 112 may be formed to include multiple non-porous layers and porous layers that are stacked in an alternating manner. In another example, buttress member 112 may be formed in a "sandwich-like" manner wherein the outer layers of buttress member 112 include porous layers and the inner layers are non-porous layers. Examples of multi-layered buttress members are disclosed in U.S. Patent Application Publication No. 2009/0001122, filed on Jun. 27, 2007, entitled "Buttress and Surgical Stapling Apparatus," the entire disclosure of which is incorporated by reference therein.

In particular, the use of non-porous layers in buttress member 112 may enhance the ability of buttress member 112 to resist tears and perforations during the manufacturing, shipping, handling, and stapling processes. In addition, the use of a non-porous layer in the surgical buttress may also retard or inhibit tissue ingrowth from surrounding tissues, and thereby acting as an adhesion barrier and inhibiting the formation of unwanted scar tissue.

In addition, at least one bioactive agent may be combined with buttress member 112. The agent may be disposed on a surface of the surgical buttress and/or impregnated therein. In these embodiments, buttress member 112 can also serve as a vehicle for delivery of the bioactive agent. The term "bioactive agent," as used herein, is used in its broadest sense and includes any substance or mixture of substances that have clinical use.

Figure 5:
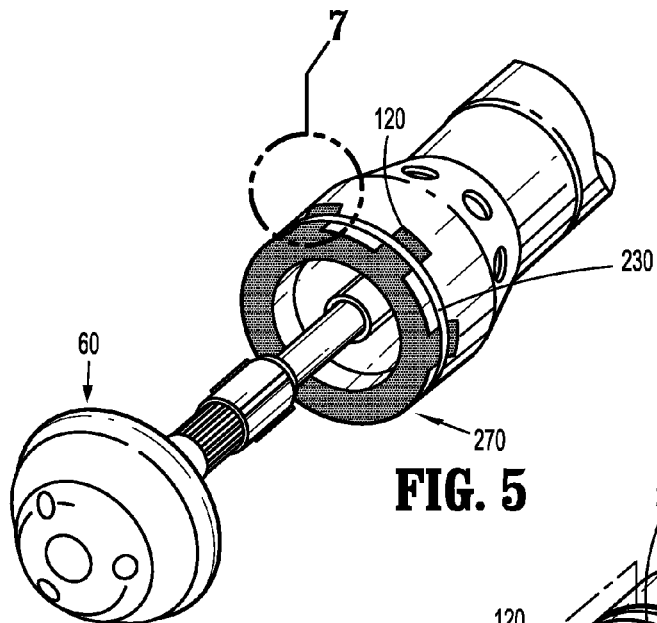
FIG. 5 is a perspective view of a head portion of a surgical stapling apparatus including a surgical buttress assembly in accordance with another embodiment of the present disclosure.
Figure 6:
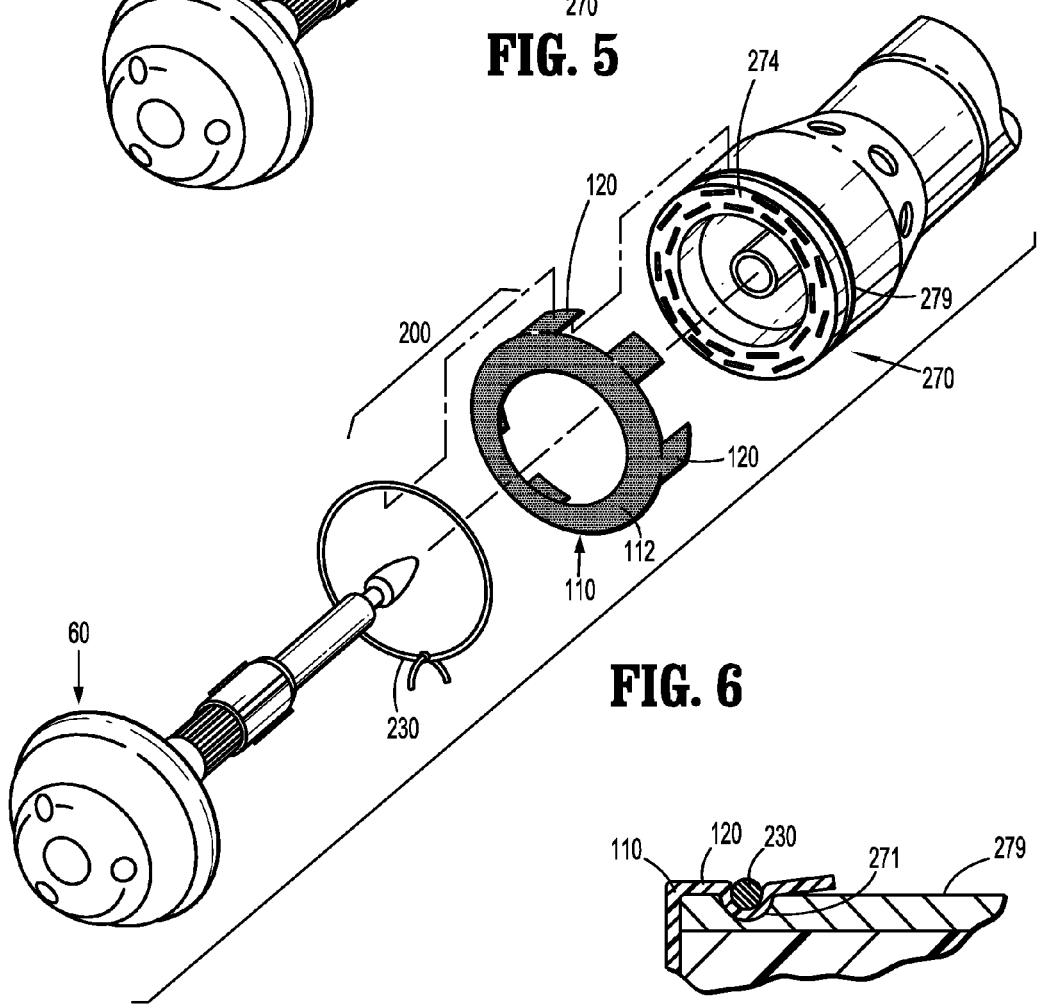
FIG. 6 is an exploded, perspective view, with parts separated, of the head portion of FIG. 5.
Figure 7:
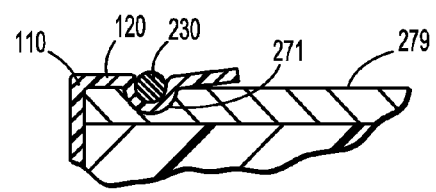
FIG. 7 is an enlarged, cross-sectional view of the area of detail indicated in FIG. 5.

With reference now to FIGS. 5-7, it is further contemplated that a surgical buttress assembly 200 may include buttress component 110 and a fastening member in the form of a suture 230. In contrast to surgical buttress assembly 100, suture 230 may be utilized to securely position buttress component 110 on a distal surface 274 of a staple cartridge assembly 270. As described hereinabove, a proximal end of each tab 120 extends across a groove 271 (FIG. 7) defined in an outer wall 279 of cartridge assembly 270 when buttress member 112 is positioned on distal surface 274 of staple cartridge assembly 270.

In use, suture 230 is wrapped around circumferentially arranged tabs 120, such that suture 230 applies radially inward force against portions of tabs 120 disposed at least partially across groove 271. In particular, staple cartridge assembly 270 defines groove 271 having an arcuate, transverse, cross-sectional profile to better accommodate suture 230 that overlies groove 271, as shown in FIG. 7. Such configuration enables buttress component 110 to be securely positioned in place with respect to staple cartridge assembly 270.

Figure 8:
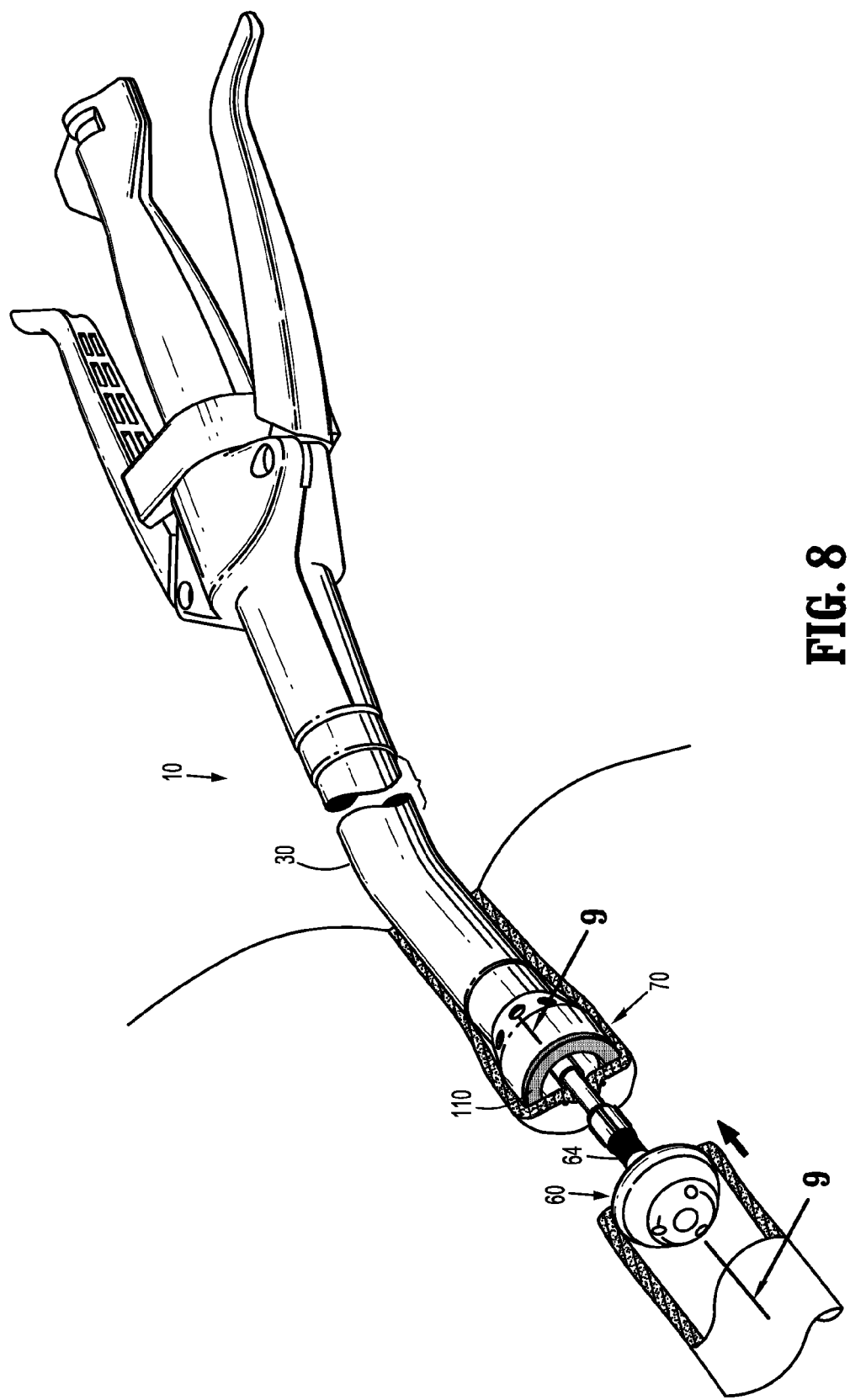
FIG. 8 is a perspective view of the annular surgical apparatus of FIG. 1 illustrating insertion of the apparatus through two hollow organ sections.
Figure 10:
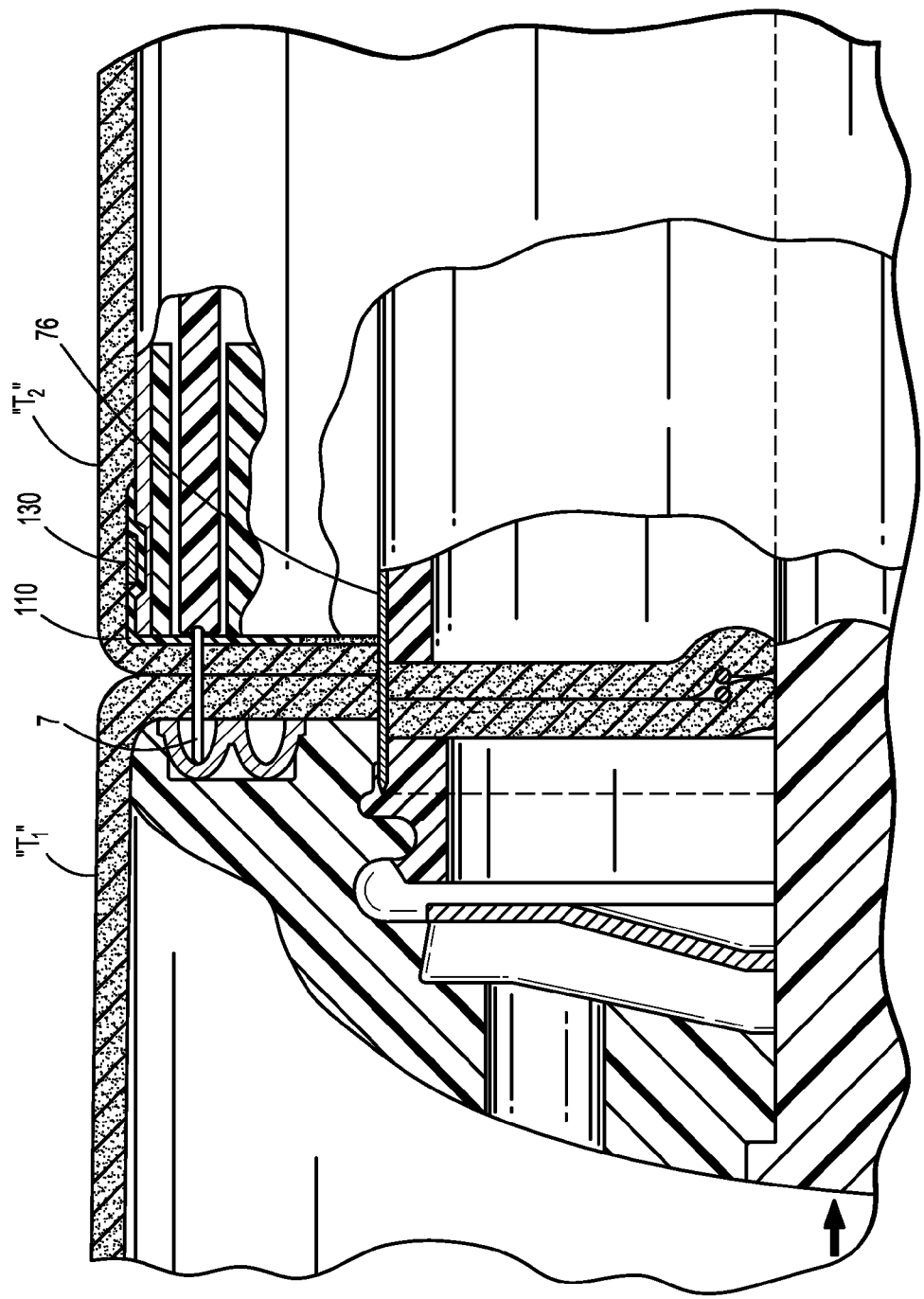
FIG. 10 is an enlarged, partial longitudinal, cross-sectional view of the head portion of the apparatus of FIG. 8, illustrating stapling and cutting of the two hollow organ sections.

With reference to FIGS. 8-10, surgical stapling apparatus 10 is shown in use in an anastomosis procedure to effect joining of, for example, two opposing intestinal sections. The anastomosis procedure is typically performed using minimally invasive surgical techniques including laparoscopic means and instrumentation. Initially, a diseased intestinal section is removed. Thereafter, anvil assembly 60 is inserted to the operative site either through a surgical incision or transanally and is positioned within the intestinal section "$T_1$." Elongate body portion 30 of surgical stapling apparatus 10, including staple cartridge assembly 70, is inserted transanally into the other intestinal section "$T_2$." The intestinal sections "$T_1$," "$T_2$" are then temporarily secured about their respective components (e.g., shaft 64 of anvil assembly 60 and the distal end of elongate body portion 30) by conventional means such as a purse string suture "P" (see FIG. 9).

Thereafter, the clinician maneuvers anvil assembly 60 until the proximal end of shaft 64 is inserted into and attached/connected to the distal end of approximation shaft 75 disposed in elongate body portion 30 of surgical stapling apparatus 10. Shaft 64 engages approximation shaft 75 to be operable as a unitary construct. Anvil assembly 60 and elongate body portion 30 are then approximated to approximate the intestinal sections "$T_1$," $T_2$." Surgical stapling apparatus 10 is then fired causing the plurality of staple pushers 9 each disposed in respective staple receiving slot 72 to eject the respective staple 7 through slot 72. Staples 7 travel through intestinal sections "$T_1$," $T_2$," as well as buttress member 112, toward anvil assembly 60, thereby effecting stapling of intestinal sections "$T_1$," $T_2$" to one another, while cylindrical knife 76 cuts a portion of tissue disposed radially inward of cylindrical knife 76 to complete the anastomosis. At this time, tabs 120 remain attached to buttress member 112 stapled to the intestinal sections "$T_1$," $T_2$" and are secured with staple cartridge assembly 70 by annular ring 130. Upon removal of surgical stapling apparatus 10 from the surgical site, the break or the line of weakening adjacent buttress member 112 facilitates detachment of tabs 120 from buttress member 112 stapled to intestinal sections "$T_1$," $T_2$."

Figure 11:
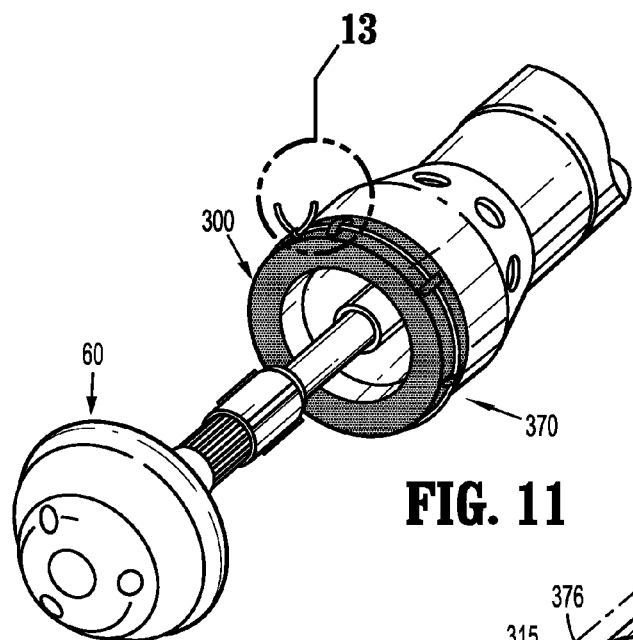
FIG. 11 is a perspective view of a head portion of a surgical stapling apparatus including a surgical buttress assembly in accordance with still another embodiment of the present disclosure.
Figure 12:
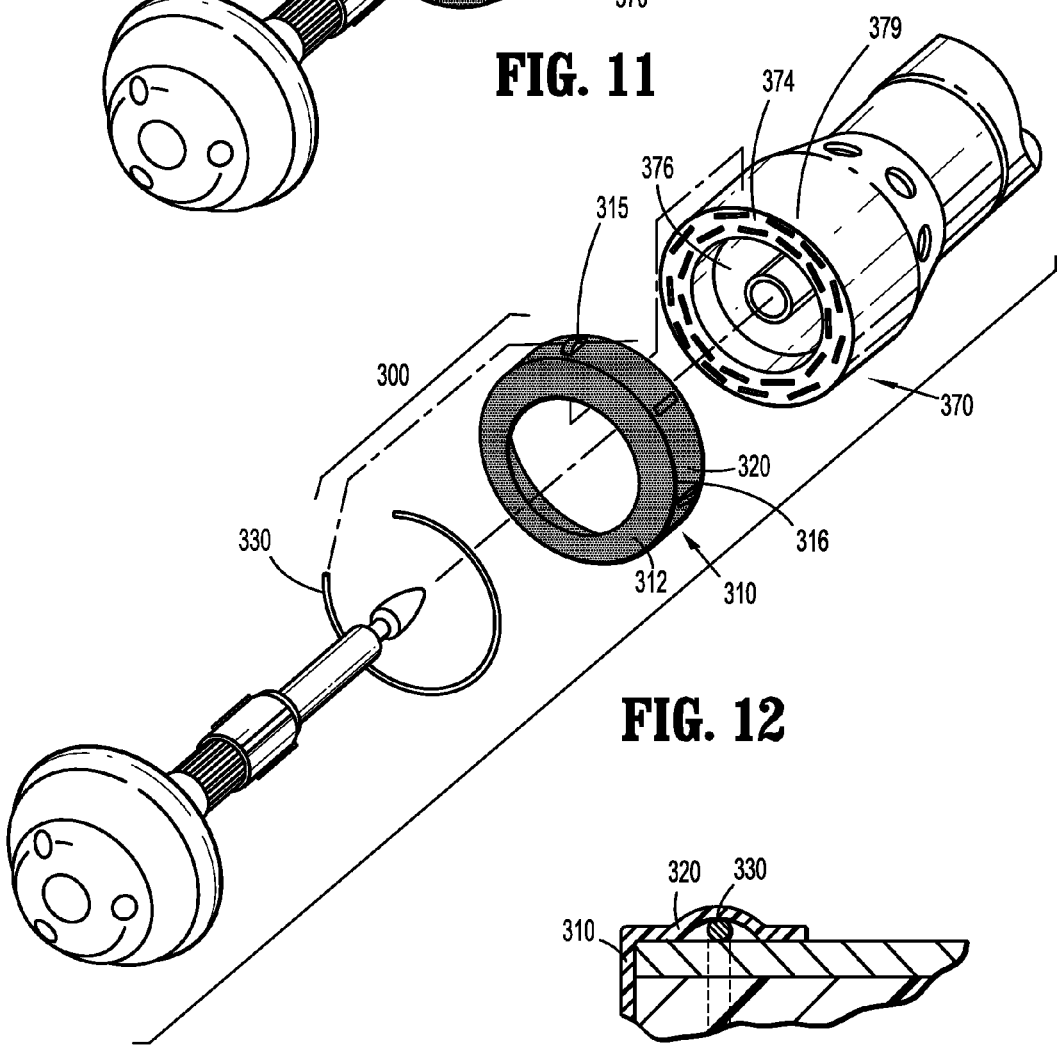
FIG. 12 is an exploded, perspective view, with parts separated, of the head portion of FIG. 11.
Figure 13:
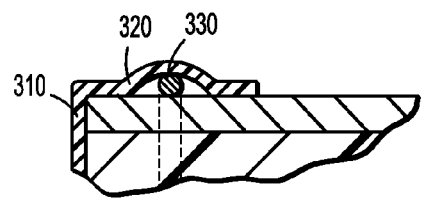
FIG. 13 is an enlarged, cross-sectional view of the area of detail indicated in FIG. 11.

With reference now to FIGS. 11-13, a buttress assembly 300 in accordance with another embodiment of the present disclosure is shown. A fastening member is in the form of a suture 330. In particular, buttress component 310 includes a buttress member 312 configured and dimensioned to be positioned on a distal surface 374 of staple cartridge assembly 370 and a rim 320 extending proximally from an outer radial edge of buttress member 312. Rim 320 engages an outer wall 379 of staple cartridge assembly 370, whereby buttress component 310 encloses distal surface 374 of staple cartridge assembly 370. A cylindrical knife 376 is disposed radially inward of buttress member 312, whereby under such a configuration severing of buttress member 312 by cylindrical knife 376 is eliminated.

Rim 320 includes a plurality of circumferentially arranged loops 315. Each loop 315 is configured and dimensioned to accommodate a suture 330 therethrough. Suture 330 is wrapped and tied around rim 320 through the plurality of loops 315 against outer wall 379 of staple cartridge assembly 370 to secure buttress component 310 on staple cartridge assembly 370. In addition, rim 320 includes a circumferentially defined break, plurality of perforations or line of weakening 316 adjacent buttress member 312, whereby buttress member 312 that is stapled to tissue may be detached from rim 320. In this manner, rim 320 that is detached from buttress member 312 remains secured to outer wall 379 of staple cartridge assembly 370 by suture 330 and is removed from the surgical site along with staple cartridge assembly 370. Alternatively, each loop 315 may be created by defining a pair of substantially adjacent slits in rim 320.

Figure 14:
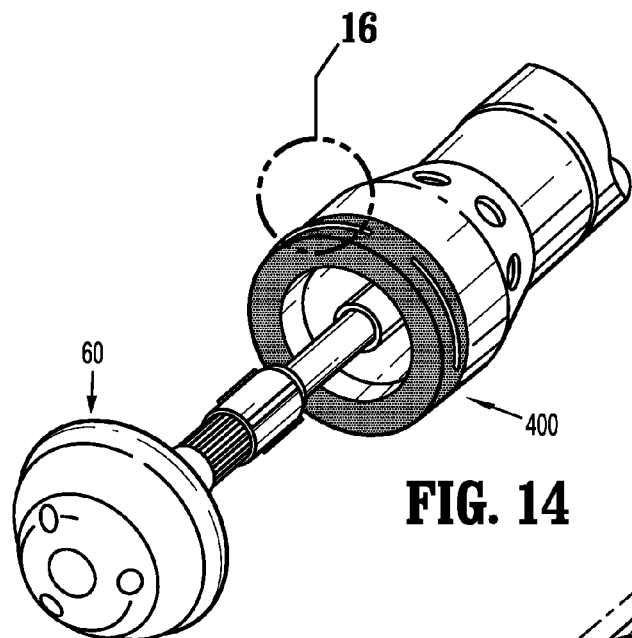
FIG. 14 is a perspective view of a head portion of a surgical stapling apparatus including a surgical buttress assembly in accordance with still another embodiment of the present disclosure.
Figure 15:
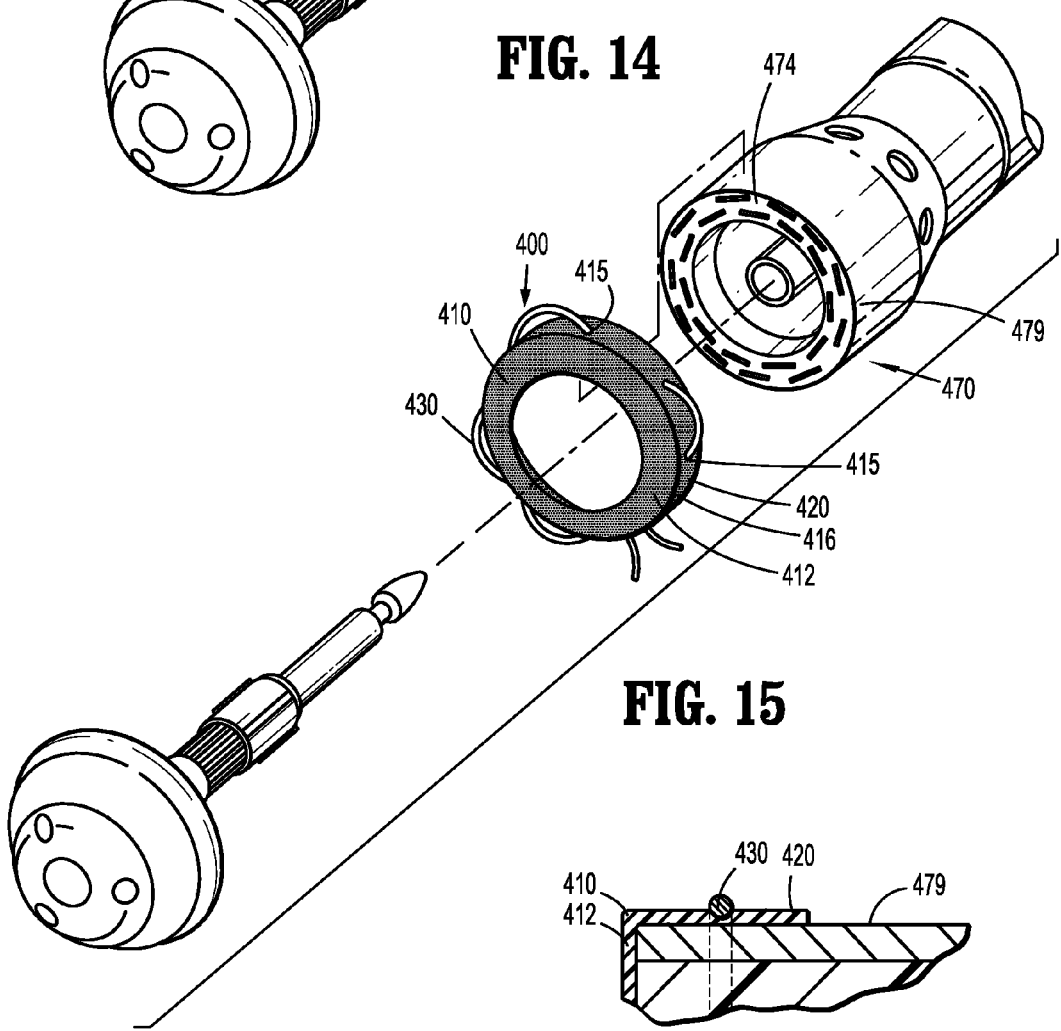
FIG. 15 is an exploded, perspective view, with parts separated, of the head portion of FIG. 14.
Figure 16:
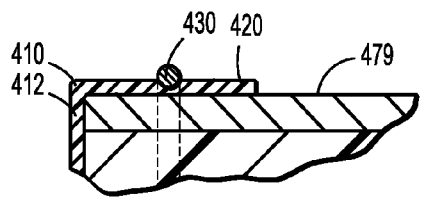
FIG. 16 is an enlarged, cross-sectional view of the area of detail indicated in FIG. 14.

With reference to FIGS. 14-16, a buttress assembly 400 in accordance with another embodiment of the present disclosure is shown. Buttress assembly 400 includes a buttress component 410 and a fastening member in the form of a suture 430. In particular, buttress component 410 includes a buttress member 412 configured and dimensioned to be positioned on a distal surface 474 of staple cartridge assembly 470 and a rim 420 extending proximally from an outer radial edge of buttress member 412. Rim 420 engages an outer wall 479 of staple cartridge assembly 470, whereby buttress component 410 encloses distal surface 474 of staple cartridge assembly 470.

In contrast to rim 320, rim 420 includes a plurality of circumferentially arranged apertures, holes or bores 415. Each bore 315 is configured and dimensioned to receive suture 430 therethrough. Suture 430 is looped and tied around rim 420 through the plurality of bores 415 to secure buttress component 410 on staple cartridge assembly 470. In addition, rim 420 includes a break 416 circumferentially defined adjacent buttress member 412, whereby buttress member 412 that is stapled to tissue may be detached from rim 420. In this manner, rim 420 that is detached from buttress member 412 is secured to outer wall 479 of staple cartridge assembly 470 and is removed from the surgical site along with staple cartridge assembly 470.

It is further contemplated that each bore 415 may include an adhesive or a gel such as, e.g., hydrogel, to improve securement of suture 430 in bore 415. In addition, it is also envisioned that suture 430 may include a plurality of, e.g., unidirectional, barbs, to improve securement of suture 430 in bores 415. Examples of barbed sutures are disclosed in U.S. patent application Ser. No. 12/361,962, filed Jan. 29, 2009, the entire content of which is incorporated herein by reference. A compound barbed suture is available commercially as V-LOC™ from Tyco Healthcare Group, LLP (dba Covidien AG, Mansfield, Mass.).

Figure 17:
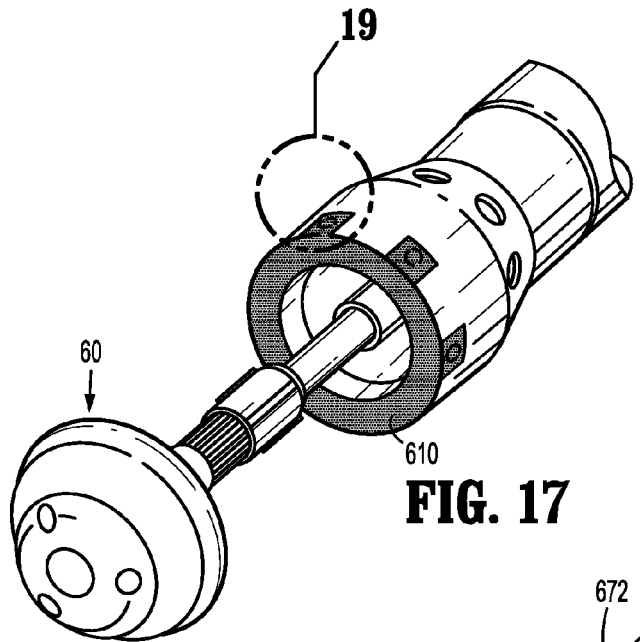
FIG. 17 is a perspective view of a head portion of a surgical stapling apparatus including a surgical buttress assembly in accordance with still yet another embodiment of the present disclosure.
Figure 18:
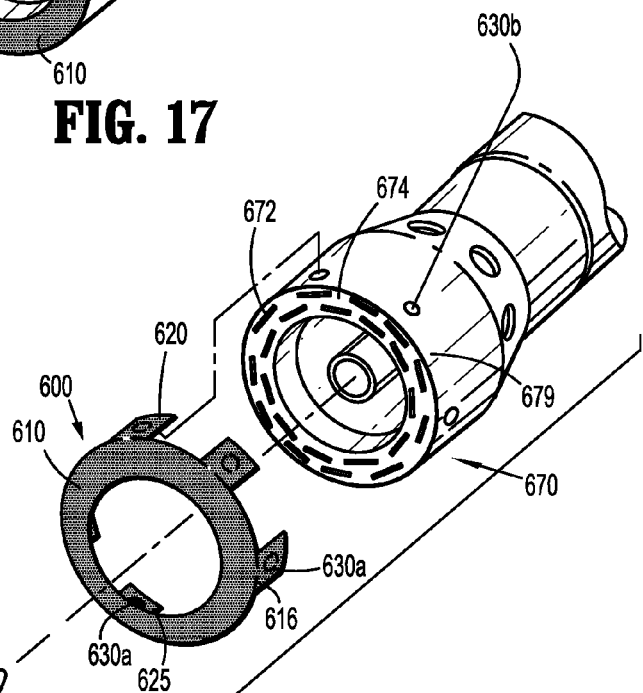
FIG. 18 is an exploded, perspective view, with parts separated, of the head portion of FIG. 17.
Figure 19:
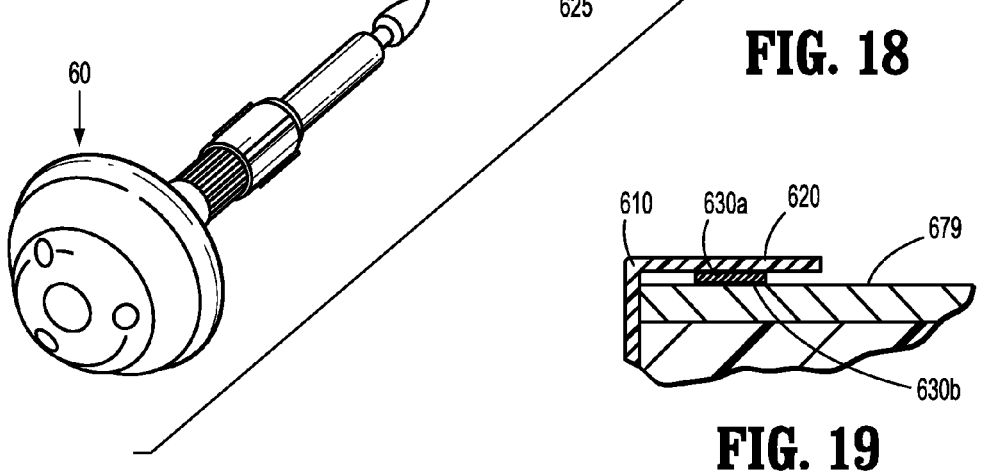
FIG. 19 is an enlarged, cross-sectional view of the area of detail indicated in FIG. 17.

With reference to FIGS. 17-19, a buttress assembly 600 in accordance with another embodiment of the present disclosure is shown. Buttress assembly 600 includes a buttress member 610 and a plurality of circumferentially arranged tabs 620 extending proximally from an outer radial edge of buttress member 610. Each tab 620 includes an attaching member 630a on an inner wall or surface 625 thereof.

Furthermore, outer wall 679 of staple cartridge assembly 670 includes a plurality of circumferentially arranged attaching members 630b corresponding to attaching members 630a on tabs 620. Attaching members 630a, 630b may include, for example, a refastenable tape or a hook and loop fastener. Alternatively, tabs 620 may include a double-sided adhesive tape to detachably position buttress assembly 600 to staple cartridge assembly 670.

In addition, it is also envisioned that each tabs 620 may include a break, perforations or a line of weakening 616, whereby buttress member 610 that is stapled to tissue may be severed or detached from tabs 620. In this manner, tabs 620 may be secured with staple cartridge assembly 670 by attaching members 630a, 630b and removed from the surgical site along with staple cartridge assembly 670.

Figure 20:
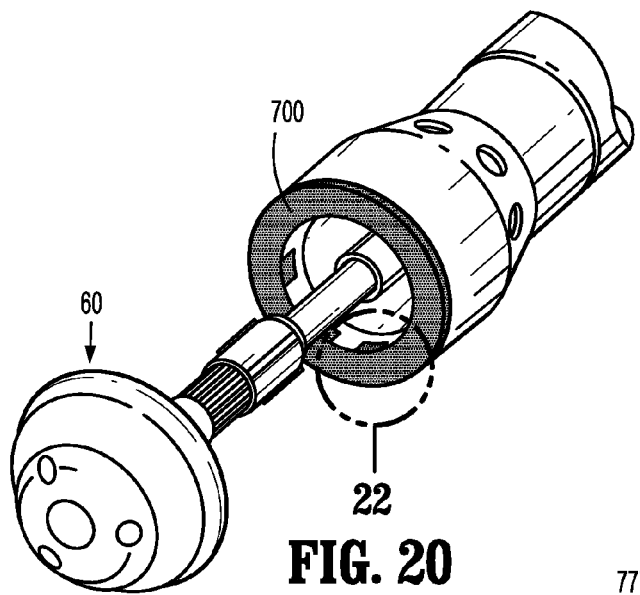
FIG. 20 is a perspective view of a head portion of a surgical stapling apparatus including a surgical buttress assembly in accordance with still yet another embodiment of the present disclosure.
Figure 21:
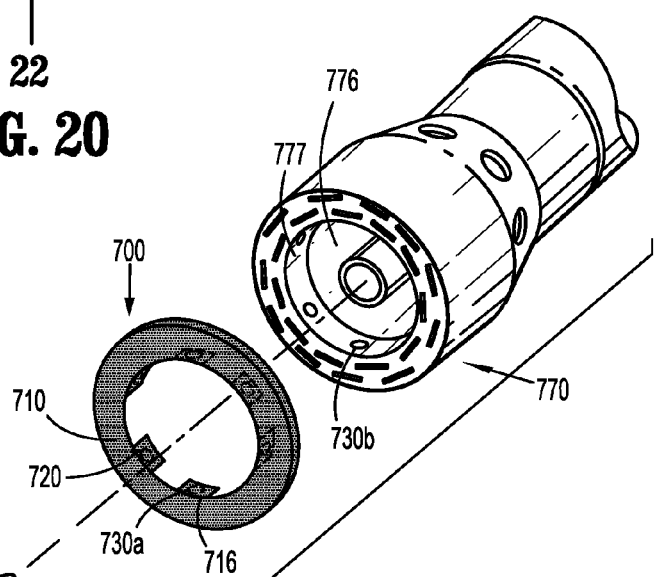
FIG. 21 is an exploded, perspective view, with parts separated, of the head portion of FIG. 20.
Figure 22:
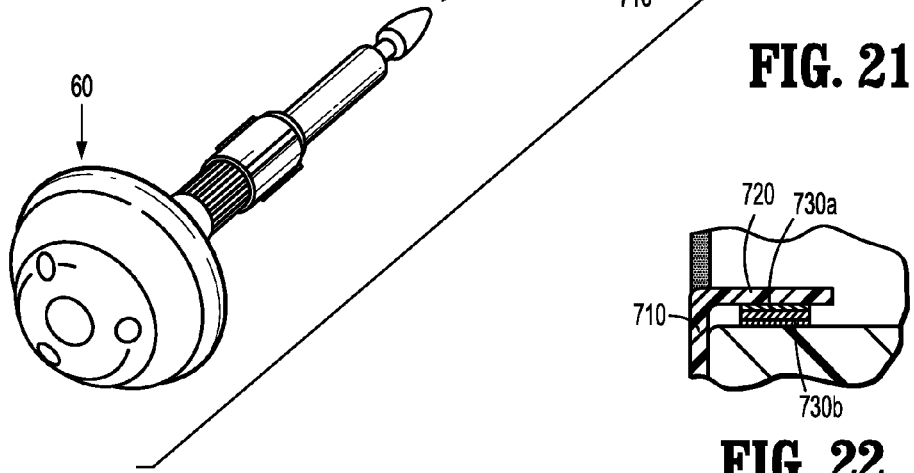
FIG. 22 is an enlarged, cross-sectional view of the area of detail indicated in FIG. 20.

With reference now to FIGS. 20-22, it is also contemplated that a buttress assembly 700 may include a buttress member 710 and a plurality of circumferentially arranged tabs 720 extending proximally from an inner radial edge of buttress member 710 that engage an inner wall 777 of staple cartridge assembly 770. In particular, each tab 720 includes an attaching member 730a on an outer wall thereof. Furthermore, inner wall 777 of staple cartridge assembly 770 includes a plurality of circumferentially arranged attaching members 730b corresponding to attaching members 730a on tabs 720. Attaching members 730a, 730b may include, for example, a refastenable tape or a hook and loop fastener.

Under such a configuration, cylindrical knife 776 is positioned radially inward of attaching members 730b circumferentially arranged on inner wall 777 of staple cartridge assembly 770 and positioned radially outward of attaching members 730a on respective outer wall of each tab 720. Under such a configuration, cylindrical knife 776 travels between attaching members 730a, 730b and severs tabs 720 from buttress member 710. In addition, tabs 720 may include a break, perforations, or a line of weakening 716 to facilitate severing of tabs 720 from buttress member 710. In this manner, buttress member 710 that is stapled to tissue may be detached from tabs 720.

Figure 23:
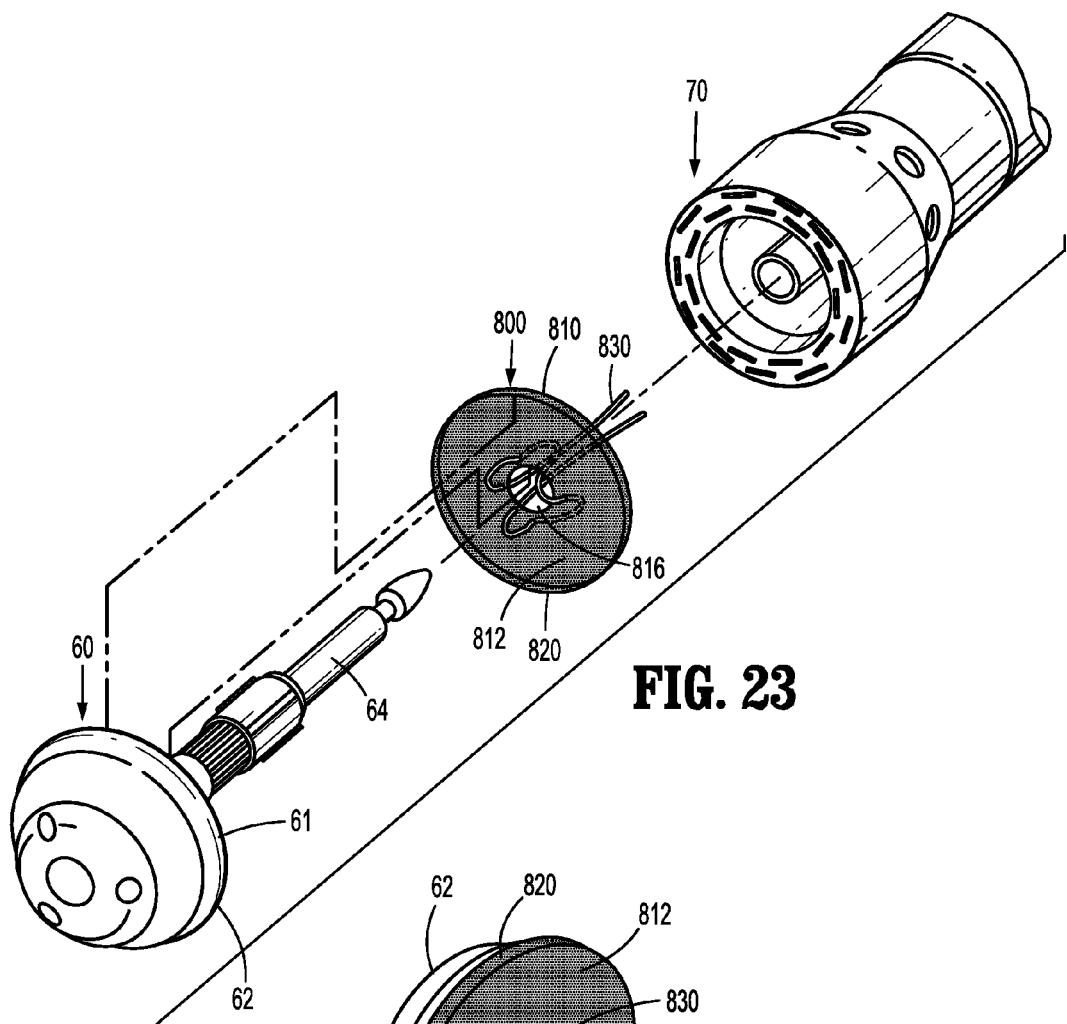
FIG. 23 is a perspective view of a head portion of a surgical stapling apparatus including a surgical buttress assembly in accordance with still another embodiment of the present disclosure, illustrating an anvil assembly and the surgical buttress assembly detached from the surgical stapling apparatus.
Figure 24:
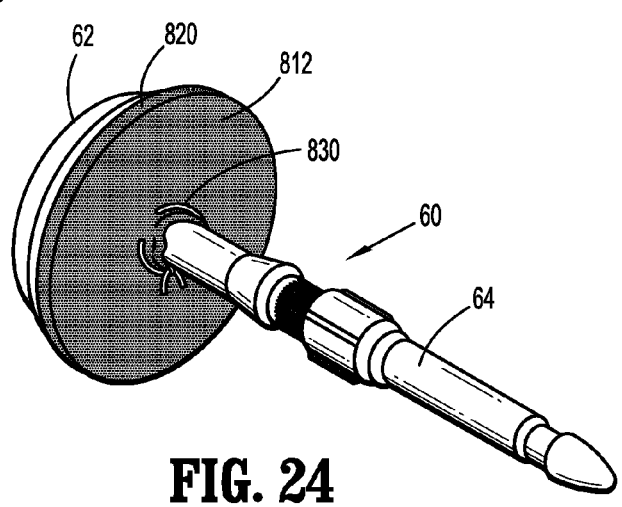
FIG. 24 is a perspective view of the anvil assembly and the surgical buttress assembly of FIG. 23 securely positioned on the anvil assembly.

With reference to FIGS. 23 and 24, a buttress assembly 800 in accordance with another embodiment of the present disclosure is shown. In contrast to buttress assemblies 100, 200, 300, 400, 600, 700, described hereinabove, buttress assembly 800 is configured and adapted to be securely positioned with anvil assembly 60. Buttress assembly 800 includes a buttress component 810. A suture 830 is used to attach the buttress component to the stapling apparatus. Buttress component 810 includes a buttress member 812 having an annular profile configured and dimensioned to be flush with an outer peripheral edge of anvil member 62 when mounted on anvil member 62 and a rim 820 extending distally from buttress member 812. In addition, rim 820 engages an outer wall 61 of anvil member 62, whereby buttress component 810 encloses a proximal surface of anvil member 62 defining the plurality of pockets for receiving and forming staples 7. Additionally, buttress member 812 defines an aperture, hole or bore 816 configured and dimensioned to receive shaft 64 of anvil assembly 60 therethrough. Bore 816 is dimensioned to provide a friction and tight fit around shaft 64. Additionally or alternatively, a suture 830 may be further utilized to securely fasten buttress member 812 to shaft 64.

Figures 25, 26:
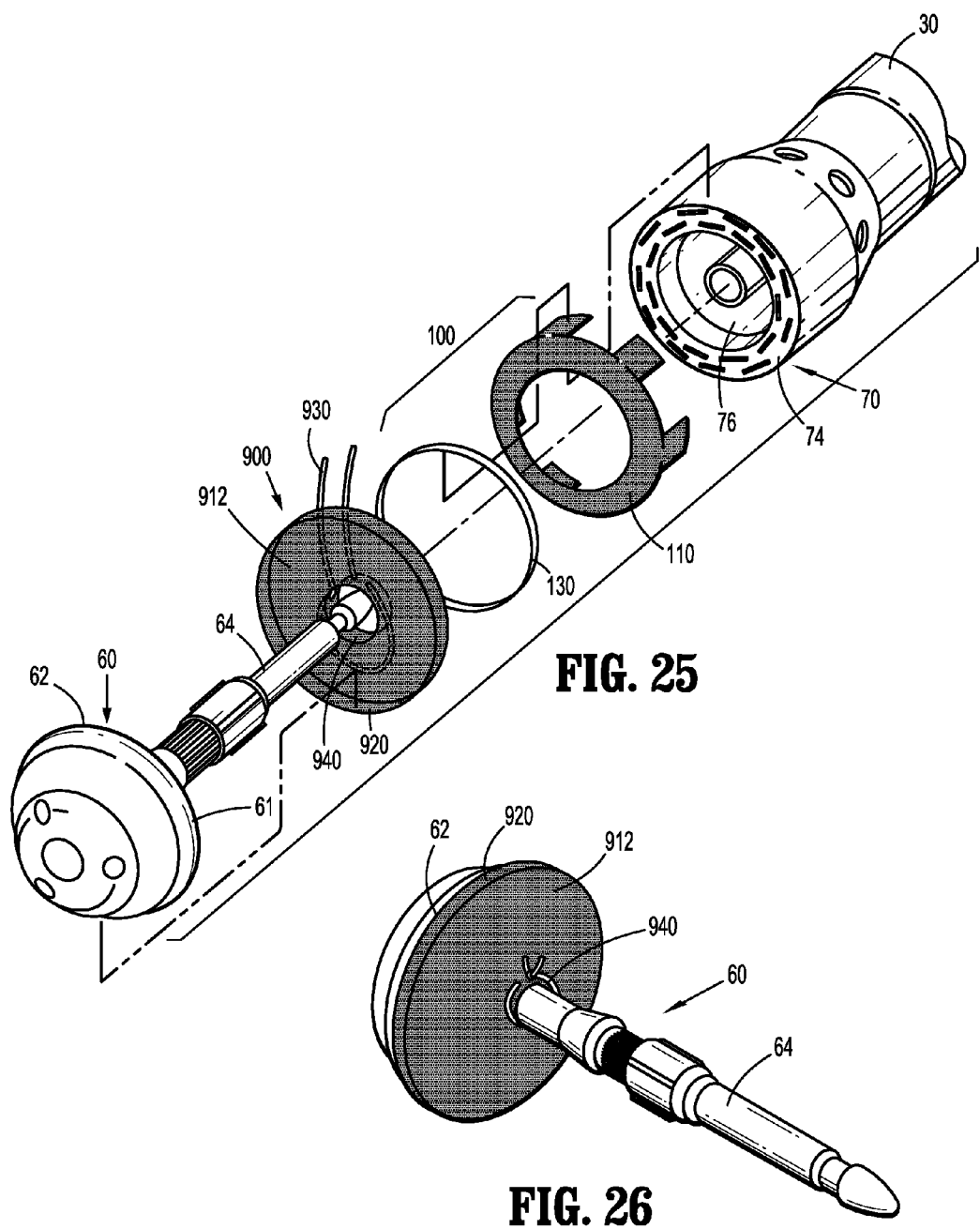
FIG. 25 is an exploded, perspective view, with parts separated, of a head assembly of a surgical stapling apparatus including a surgical buttress assembly in accordance with still yet another embodiment of the present disclosure.
FIG. 26 is a perspective view of an anvil assembly and the surgical buttress assembly of FIG. 25 securely positioned on the anvil assembly.

With reference to FIGS. 25 and 26, in an alternate embodiment a buttress assembly 900 includes a buttress member 912 radially extending between an outer rim 920 and an inner rim 940. In particular, outer rim 920 is configured and dimensioned to engage outer wall 61 of anvil member 62 and inner rim 940 is configured and dimensioned to provide a tight or friction fit against shaft 64 of anvil assembly 60. In this manner, radial and longitudinal movement of buttress assembly 900 with respect to anvil assembly 60 is minimized. In addition, a fastening member in the form of a suture 930 is wrapped or tied around inner rim 940 of buttress member 912 against shaft 64 of anvil assembly 60 to further secure buttress assembly 900 on anvil assembly 60.

With continued reference to FIG. 25, buttress assembly 900 may be used in conjunction with buttress assembly 100 that is positionable on distal surface 74 of staple cartridge assembly 70, as well as any one of buttress assemblies 200, 300, 400, 600, 700, described hereinabove. Buttress assembly 100 is positioned radially outward of cylindrical knife 76. As such, upon actuation of handle members 22, the entire buttress member 112 is stapled to tissue to reinforce the tissue, and severing of buttress member 112 by cylindrical knife 76 is eliminated. However, cylindrical knife 76 cores a portion of buttress member 912 along with inner rim 940 and suture 930 wrapped and tied around inner rim 940, to free such portions from a portion of buttress member 912 that is also stapled to tissue. The use and operation of assemblies 200, 300, 400, 600, 700, 800, 900 are substantially similar to the use and operation of buttress assembly 100 described hereinabove, and thus will not be described further herein.

Although the illustrative embodiments of the present disclosure have been described herein with reference to the accompanying drawings, the above description, disclosure, and figures should not be construed as limiting, but merely as exemplifications of particular embodiments. For example, buttress assembly 900 including buttress member 912 radially extending between inner rim 940 and outer rim 920 may be tailored for use on distal surface 74 of staple cartridge assembly 70. In addition, buttress assembly 900 may further utilize an annular ring 130 or suture 330 to secure outer rim 920 of buttress assembly 900 against outer wall 61 of anvil assembly 60. It is to be understood, therefore, that the disclosure is not limited to those precise embodiments, and that various other changes and modifications may be effected therein by one skilled in the art without departing from the scope or spirit of the disclosure.

What is claimed is:

1. An apparatus for joining two hollow organ sections with an annular array of surgical staples, the apparatus comprising:
   a staple cartridge component including a plurality of surgical staples arranged in an annular array, the staple cartridge component including an outer wall defining a circumferential groove therein;
   an anvil component movable relative to the staple cartridge component between spaced apart and approximated positions to adjustably clamp the organ sections between the staple cartridge and anvil components;
   a buttress component configured and dimensioned to be positioned on a distal surface of the staple cartridge component, the buttress component including a buttress member and a plurality of circumferentially arranged tabs extending proximally from the buttress member, each tab having a length such that the tab extends across the circumferential groove of the staple cartridge component when the buttress member overlies a tissue facing surface of the staple cartridge component; and
   a fastening member configured and dimensioned to engage the plurality of circumferentially arranged tabs into the circumferential groove of the staple cartridge component to securely position the buttress component on the staple cartridge component.

2. The apparatus according to claim 1, wherein the buttress member has an annular configuration, the buttress member concentrically disposed in a juxtaposed relation with the plurality of surgical staples.

3. The apparatus according to claim 1, wherein the fastening member is an annular ring configured and dimensioned to apply inward force to the plurality of circumferentially arranged tabs against the outer wall of the staple cartridge component.

4. The apparatus according to claim 1, wherein the fastening member is a suture tied around the plurality of circumferentially arranged tabs against the outer wall of the staple cartridge component.

5. The apparatus according to claim 1, wherein the fastening member is in registration with the circumferential groove.

6. The apparatus according to claim 1, further comprising a knife member concentrically arranged in the staple cartridge component and with the buttress member, the knife member movable relative to the staple cartridge component.

7. The apparatus according to claim 6, wherein the buttress member is configured to be disposed radially outward of the knife member.

8. The apparatus according to claim 1, wherein the plurality of circumferentially arranged tabs each define a line of weakening adjacent the buttress member to enable detachment of the buttress member from the plurality of tabs.

* * * * *